(12) United States Patent
Haake et al.

(10) Patent No.: US 10,370,728 B2
(45) Date of Patent: Aug. 6, 2019

(54) ANTIBIOTIC SUSCEPTIBILITY TESTING USING PROBES FOR PRERIBOSOMAL RNA

(71) Applicants: THE REGENTS OF THE UNIVERSITY OF CALIFORNIA, Oakland, CA (US); THE UNITED STATES OF AMERICA REPRESENTED BY THE DEPARTMENT OF VETERANS AFFAIRS, Washington, DC (US)

(72) Inventors: David A. Haake, Culvert City, CA (US); Colin Halford, Los Angeles, CA (US); Jane T. Babbitt, Culver City, CA (US); Bernard M. Churchill, Pacific Palisades, CA (US)

(73) Assignees: THE REGENTS OF THE UNIVERSITY OF CALIFORNIA, Oakland, CA (US); THE UNITED STATES OF AMERICA REPRESENTED BY THE DEPARTMENT OF VETERANS AFFAIRS, Washington, DC (US)

(*) Notice: Subject to any disclaimer, the term of this patent is extended or adjusted under 35 U.S.C. 154(b) by 511 days.

(21) Appl. No.: 14/398,725

(22) PCT Filed: May 3, 2013

(86) PCT No.: PCT/US2013/039574
§ 371 (c)(1),
(2) Date: Nov. 3, 2014

(87) PCT Pub. No.: WO2013/166460
PCT Pub. Date: Nov. 7, 2013

(65) Prior Publication Data
US 2015/0104789 A1   Apr. 16, 2015

Related U.S. Application Data

(60) Provisional application No. 61/643,009, filed on May 4, 2012.

(51) Int. Cl.
*C12Q 1/689* (2018.01)

(52) U.S. Cl.
CPC ....... *C12Q 1/689* (2013.01); *C12Q 2600/106* (2013.01)

(58) Field of Classification Search
CPC ...................................... C12Q 1/689
See application file for complete search history.

(56) References Cited

U.S. PATENT DOCUMENTS

| 5,712,095 A | 1/1998 | Britschgi et al. |
| 5,770,373 A | 6/1998 | Britschgi et al. |

(Continued)

FOREIGN PATENT DOCUMENTS

| EP | 0531798 B2 | 12/2003 |
| WO | WO9905159 A2 | 2/1999 |

(Continued)

OTHER PUBLICATIONS

Britschgi, T.B. et al. Molecular and Cellular Probes 9:19 (1995).*

(Continued)

*Primary Examiner* — Diana B Johannsen
(74) *Attorney, Agent, or Firm* — Karen S. Canady; canady + lortz LLP

(57) ABSTRACT

Described are probes and methods for detecting antibiotic susceptibility of a specimen. The method comprises contacting the specimen with an oligonucleotide probe that specifically hybridizes with a target nucleic acid sequence region of ribosomal RNA. The target sequence is at the junction between a pre-ribosomal RNA tail and mature ribosomal RNA of 23S or 16S rRNA. Performing the (Continued)

method in the presence and absence of an antibiotic permits detection of antibiotic susceptibility.

17 Claims, 13 Drawing Sheets

Specification includes a Sequence Listing.

(56) References Cited

U.S. PATENT DOCUMENTS

| | | | |
|---|---|---|---|
| 6,348,314 | B1 | 2/2002 | Prudent et al. |
| 6,391,558 | B1 | 5/2002 | Henkens et al. |
| 6,582,908 | B2 | 6/2003 | Fodor et al. |
| 7,002,005 | B1 | 2/2006 | Berghof |
| 9,512,474 | B2 * | 12/2016 | Seone .................... C12Q 1/689 |
| 2002/0123048 | A1 | 9/2002 | Gau et al. |
| 2006/0154257 | A1 | 7/2006 | Mitchell |
| 2007/0031843 | A1 | 2/2007 | Bentwich et al. |
| 2008/0199863 | A1 | 8/2008 | Haake et al. |

FOREIGN PATENT DOCUMENTS

| | | | | |
|---|---|---|---|---|
| WO | WO-9947706 | A1 * | 9/1999 | ........... C12Q 1/6874 |
| WO | WO2012027302 | A2 | 3/2002 | |
| WO | WO2005017202 | A2 | 2/2005 | |
| WO | WO2007112965 | A1 | 10/2007 | |

OTHER PUBLICATIONS

Halford, C. et al. Antimicrobial Agents and Chemotherapy 57(2):936 (Feb. 2013; online Dec. 10, 2012).*
Cangelosi, G.A. et al. Antimicrobial Agents and Chemotherapy 40(8):1790 (Aug. 1996).*
Watkins, N.E. et al. Nucleic Acids Research 33(19):6258 (Nov. 2005).*
Abd-Elsalam, Kamel A. et al., Bioinformatic Tools and Guidelines for PCR Primer Design, pp. 91-95, vol. 2, No. 5, Publisher: African Journal of Biotechnology, 2003.
Barczak, Amy K. et al., RNA signatures allow rapid identification of pathogens 1-16,18 and antibiotic susceptibilities, Apr. 17, 2012, pp. 6217-6222, vol. 109, No. 16, Publisher: PNAS.
Cangelosi, G.A. et al., Depletion of pre-16S rRNA in starved *Escherichia coli* cells, 1997, pp. 4457-4463, vol. 179, No. 14, Publisher: Journal of Bacteriology.
Database EMBL-EBI, Sequence:FJ444805.1: *Pseudomonas* sp. EPB:P3:RCL 23S 4, Oct. 6, 2009, Publisher: http://www.ebi.ac.uk/ena/data/view/FJ444805.
King T.C., et al., S1 nuclease mapping analysis of ribosomal RNA processing in wild type and processing deficient *Escherichia coli*, 1983, pp. 12034-12042, vol. 258, Publisher: J. Biol. Chem.
Maity B. et al.,Development of a macroarray based on 16S-23S rDNA probe 3,7,8,17 hybridization for rapid diagnosis of human pathogenic bacteria, 2008, pp. 448-455, vol. 7, Publisher: Indian Journal of Biotechnology.
Sekiya Takao, et al., Sequence of the distal tRNA 1Asp gene and the transcription termination signal in the *Escherichia coli* ribosomal RNA operon rrnF(or G), pp. 3809-3827, vol. 8, No. 17, Publisher: Nucleic Acids Research, 1980.
Walker John M., et al., Probe Design, Production, and Applications. Molecular Biomethods Handbook, 2008, Publisher: Humana Press.
International Search Report and Written Opinion from corresponding international application PCT/US13/39574, dated Aug. 29, 2013.
Bottger et al., "Structural Basis for Selectivity and Toxicity of Ribosomal Antibiotics", EMBO Reports, Nature Publishing Group, London, GB, vol. 2, No. 4, Apr. 1, 2001, pp. 318-323, XP002437596.
Bottger et al., "Antimicrobial Agents Targeting the Ribosome: The Issue of Selectivity and Toxicity—Lessons to Be Learned" CMLS Cellular and Molecular Life Sciences, Birkhauser-Verlag, BA, vol. 64, No. 7-8, Feb. 13, 2007, pp. 791-795, XP019511482.
Elsholz, B. "Automated detection and quantitation of bacterial RNA by using electrical microarrays", Anal. Chem, Jul. 15, 2006, 78: 4794-4802.
Fuchs, B.M., "Flow cytometric analysis of the in situ accessibility of . . . probes", Applied & Environmental Microbiology, Dec. 1998, 64(12):4973-4982.
Gau, J., "A MEMS based amperometric detector for *E. coli* bacteria using self-assembled monolayers", Biosensors & Bioelectronics, 2001, 16: 745-755.
Liao, et al., "Development of an advanced electrochemical . . . detection", J of Molecular Diagnostics, Apr. 1, 2007, 9: 158-168.
Doehlsgaard Jacob et al., "The Bacterial Ribosome as a Target for Antibiotics", Nature Reviews, Microbiology, Nature Publishing Group, GB, vol. 3, No. 11, Nov. 1, 2005, pp. 870-881, XP009074118.
Spratt, Brian G. et al. "Distinct Penicillin Binding Proteins Involved in the Division, Elongation, and Shape of *Escherichia coli* K12", PNAS, Aug. 1975, vol. 72, No. 8, 2999-3003.
Sutcliffe et al., "Improving on Nature: Antibiotics That Target Ribosome", Current Opinion in Microbiology, Current Biology Ltd, GB, vol. 8, No. 5, Oct. 1, 2005, pp. 534-542, XP027848253.
Extended European Search Report dated Nov. 26, 2015 for corresponding European Applican 13784842.0 (EP 2844762).
International Search Report and Written Opinion dated Nov. 3, 2014, from International Application No. PCT/US2014/047684, filed Jul. 22, 2014 (WO2015013324).

* cited by examiner

ANTIBIOTIC SUSCEPTIBILITY TESTING USING PROBES FOR PRERIBOSOMAL RNA

This application claims the benefit of U.S. provisional patent application No. 61/643,009, filed May 4, 2012, the entire contents of which are incorporated herein by reference.

STATEMENT REGARDING FEDERALLY SPONSORED RESEARCH

This invention was made with Government support of Grant No. AI075565, awarded by the National Institutes of Health. The Government has certain rights in the invention. This work was supported by the U.S. Department of Veterans Affairs, and the Federal Government has certain rights in the invention.

TECHNICAL FIELD OF THE INVENTION

The present invention relates generally to materials and methods for testing and detection of antibiotic susceptibility in specimens of bodily fluid and other samples. The invention also relates to materials and methods for monitoring the physiological state of bacterial cultures.

BACKGROUND

There is an urgent need for the development of rapid and convenient methods for detection and identification of bacterial pathogens in clinical specimens to guide diagnosis and treatment of infectious diseases. Antibiotic therapy is based on identification of the pathogen and its antibiotic sensitivity. Treatment should not be delayed due to the seriousness of the disease, and thus is often started before this information is available. The effectiveness of individual antibiotics varies with the resistance of the bacterial pathogen to the antibiotic. Therapeutic outcomes can be significantly improved by the availability of a rapid assay for antibiotic susceptibility.

There remains an urgent need for the development of rapid and convenient methods for detection and testing of antibiotic susceptibility. The present invention addresses this need and others, as described below.

SUMMARY

The invention provides a method for determining whether a sample of bacteria of interest is susceptible to an antibiotic agent. In one embodiment, the method comprises contacting a probe that specifically binds to a target sequence of ribosomal ribonucleic acid RNA (rRNA), more specifically, pre-ribosomal RNA (prRNA), of the bacteria of interest. In one embodiment, the target sequence comprises the junction, or splice site, between prRNA and mature ribosomal RNA (mRNA). The probe can be a single probe or a pair of probes, such as a capture probe and a detector probe. In one embodiment, the probe is a single probe that specifically hybridizes to target sequence spanning the prRNA-mRNA splice site. In another embodiment, the probe is a pair of probes that, collectively, specifically hybridize to target sequence spanning the prRNA-mRNA splice site. For example, each of the probes can hybridize to one side of the prRNA-mRNA splice site and together the two probes hybridize to a contiguous length of target sequence of prRNA that spans the splice site. The probe is contacted with the sample both in the presence and in the absence of the antibiotic agent. A reduced amount of probe hybridization in the presence of the antibiotic agent relative to the amount of probe hybridization in the absence of the antibiotic agent is indicative of the susceptibility of the sample to antibiotic.

In another embodiment, the method comprises contacting a specimen obtained from the sample of bacteria with an oligonucleotide probe or pair of probes in the absence of the agent. In one embodiment, the probe or pair of probes specifically hybridizes to a target sequence over the full length of the target sequence, wherein the target sequence consists of 25-35 contiguous nucleotides of bacterial ribosomal RNA (rRNA) spanning a splice site between a pre-ribosomal RNA (prRNA) tail and mature ribosomal RNA (mRNA). The method further comprises contacting a specimen obtained from the sample with the probe or pair of probes in the presence of the antibiotic agent; and detecting the relative amounts of probe hybridization to the target sequence in the specimens under the two contacting conditions. The sample is identified as susceptible to antibiotic treatment if the amount of probe hybridization to the target sequence in the presence of antibiotic is reduced by at least 80% relative to the amount of probe hybridization to the target sequence in the absence of antibiotic. Optionally, the method further comprises inoculating the specimen into a growth medium prior to the contacting steps.

The bacterial rRNA is typically 23S rRNA, or it can be 16S rRNA. The oligonucleotide probe or probes are typically each between about 10 to 50 nucleotides in length. In some embodiments, the probes are 12-30 nucleotides in length, while in other embodiments, they range in length from 14-20 nucleotides in length. Optionally, the oligonucleotide probe is labeled with a detectable marker. Representative markers include, but are not limited to, a fluorescent label, a radioactive label, a luminescent label, an enzyme, biotin, thiol or a dye. The detecting step of the method can comprise an optical, electrochemical or immunological assay.

In one embodiment, the method further comprises lysing the bacteria under conditions that release prRNA from the bacteria prior to the contacting steps. Thus, the sample can be prepared with a lysis agent present. Preferably, the lysis agent is selected so as to release prRNA but without damaging the target site. The targeting of the prRNA-mRNA splice site means that the method can be performed without pre-treatment of the specimen to deplete prRNA prior to the contacting of probe with the sample, and without spliced prRNA tails interfering with the measurement. The ability to perform the method without such pre-treatment facilitates rapid processing of the susceptibility determination.

Antibiotic agents for susceptibility testing include, but are not limited to, Rifampicin, Chloramphenicol, aminoglycosides, quinolones, or beta-lactam antibiotics. In addition, novel or candidate antibiotic agents can be tested for efficacy using the methods described herein. In some embodiments, the method is used to guide diagnosis and treatment of a subject from whom the specimen containing bacteria has been obtained. For example, once the method has been employed to identify the antibiotic, or class of antibiotic, to which the specimen is susceptible, the method can further comprise administering the antibiotic to the subject.

A method for determining the antibiotic efficacy of a candidate antibiotic agent can comprise contacting a specimen obtained from the sample with an oligonucleotide probe or pair of probes in the absence of the agent, wherein the probe or pair of probes specifically hybridizes to a target sequence over the full length of the target sequence, wherein the target sequence comprises 25-35 contiguous nucleotides of bacterial ribosomal RNA (rRNA) spanning a splice site between pre-ribosomal RNA (prRNA) tail and mature ribosomal RNA (mrRNA), contacting a specimen obtained from the sample with the probe or pair of probes in the presence of the agent; and detecting the relative amounts of probe hybridization to the target sequence in the specimens. The agent is identified as effective if the amount of probe hybridization to the target sequence in the presence of the agent is reduced by at least 80% relative to the amount of probe hybridization to the target sequence in the absence of the agent.

The invention additionally provides a device for detecting pre-rRNA in a bacterial sample. The device, in one embodiment, comprises an oligonucleotide probe immobilized on a solid support, wherein the oligonucleotide probe is between about 10 to 50 nucleotides in length and is capable of selectively hybridizing to a target sequence over the full length of the target sequence. The target sequence typically comprises 25-35 contiguous nucleotides of bacterial ribosomal RNA (rRNA) spanning a splice site between pre-ribosomal RNA (prRNA) tail and mature ribosomal RNA (mrRNA). The solid support is typically an electrode or a membrane. Also contemplated is an ELISA well, or optical surface.

The invention further comprises a kit that can be used in practising the methods described herein. The kit can comprise an oligonucleotide probe or a pair of oligonucleotide probes selected from those described herein. The probes can optionally be labelled with a detectable marker. The kit can further comprise one or more containers for housing the probe(s) and other reagents for use with the method.

The invention also provides a method for monitoring the growth rate of a bacterial culture. The method comprises contacting a specimen obtained from the culture with a probe or pair of probes that specifically hybridizes to a target sequence over the full length of the target sequence, wherein the target sequence comprises 25-35 contiguous nucleotides of bacterial ribosomal RNA (rRNA) spanning a splice site between pre-ribosomal RNA (prRNA) tail and mature ribosomal RNA (mrRNA). The method further comprises detecting the amount of probe hybridization to the target sequence in the specimen of (a) relative to an earlier time point; and/or relative to a control that either lacks or includes a growth medium component to be tested. The culture is identified as growing, or in a log phase of growth, if the amount of probe hybridization to the target sequence at the subsequent time point is increasing relative to the amount of probe hybridization to the target sequence at the earlier time point.

BRIEF DESCRIPTION OF THE FIGURES

FIG. 3A: Changes in mature rRNA, pre-rRNA, and their ratio were measured in overnight (ON) cultures that were subsequently inoculated into fresh MH growth medium and incubated for 7 hours at 37° C. FIG. 3B: Comparison of the mature/pre-RNA ratio and growth rate during different phases of growth. The growth rate curve is a weighted average determined from the change in CFU during each 30 min time period. Errors bars estimated the standard deviation.

FIG. 4A: Correlation between the cell volume and rRNA copy number per cell at densities below OD600 nm≤1.0. FIG. 4B: Electron micrographs demonstrating progressively smaller cells over incubation time from log phase (2.5 hrs) to stationary phase (7 hrs). Errors bars estimated the standard deviation.

DETAILED DESCRIPTION

Figure 1:
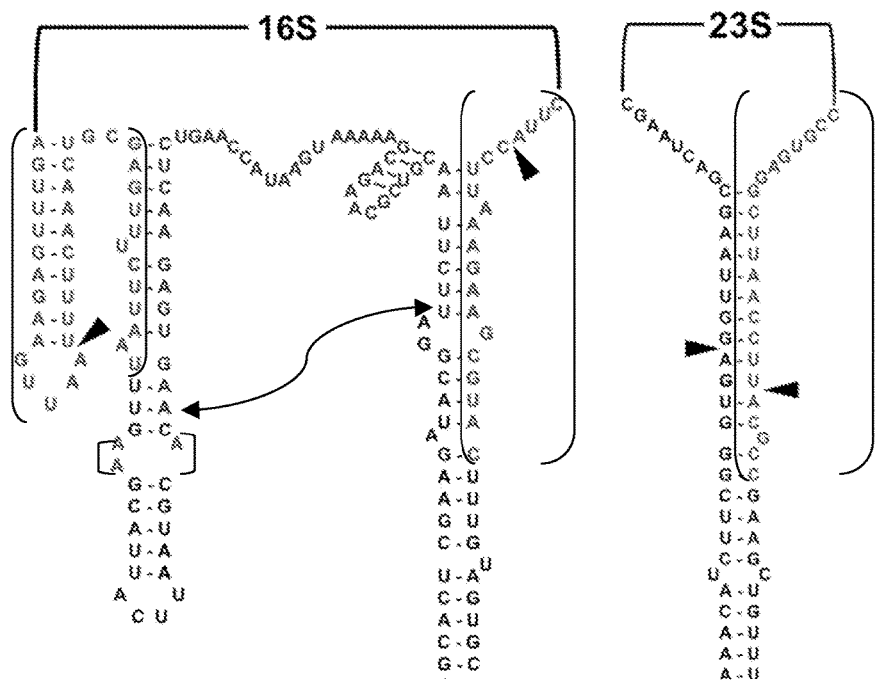
FIG. 1. Regions targeted by pre-rRNA probe pairs. The structures of the 16S (SEQ ID NO: 49) and 23S (SEQ ID NO: 50) pre-rRNA molecules are shown, including locations of mature rRNA termini (pointers) and regions targeted by electrochemical sensor probe pairs for the 16S 5' tail (sequence between two heads of double-headed arrow) and 16S and 23S splice sites (between brackets).

Ribosomal RNA is an excellent target molecule for pathogen detection systems because of its abundance in the bacterial cell and because of the accessibility of species-specific signature sequences to probe hybridization (5). (Numbers in parentheses correspond to numbers in list of cited references at the end of the Detailed Description.) When combined with sensitive surface chemistry methods to minimize nonspecific background signals, such rRNA probe hybridization sensors are able to detect as few as 100 bacteria per ml (2, 7, 16). Estimations of bacterial density are possible because, within the dynamic range of the assay, there is a log-log correlation between the concentration of target rRNA molecules in the bacterial lysate and the amperometric current amplitude generated by the electrochemical sensor assay (9, 11). The accuracy of bacterial quantitation methods based on rRNA detection is mitigated by variations in the number of rRNA molecules per cell depending on the cell type and bacterial growth phase. In *E. coli*, the rRNA copy number per cell has been estimated to vary from as high as 72,000 during log phase to less than 6,800 during stationary phase (1).

Precursor ribosomal RNA (pre-rRNA) is an intermediate stage in the formation of mature ribosomal RNA (rRNA) and is a useful marker for cellular metabolism and growth rate. In one embodiment, the invention provides an electrochemical sensor assay for Escherichia coli pre-rRNA involving hybridization of capture and detector probes with tail sections that are spliced away during rRNA maturation. A ternary self-assembled monolayer (SAM) prepared on gold electrodes surfaces by co-assembling of thiolated capture probes with hexanedithiol and post-treatment with 6-mercapto-1-hexanol minimized background signal and maximized the signal-to-noise ratio. Inclusion of internal calibration controls allowed accurate estimation of the pre-rRNA copy number per cell. As expected, the ratio of pre-rRNA to mature rRNA was low during stationary phase and high during log phase. Pre-rRNA levels were highly dynamic, ranging from 2 copies per cell during stationary phase to ~1200 copies per cell within 60 min of inoculation into fresh growth medium. Specificity of the assay for pre-rRNA was validated using rifampicin and chloramphenicol, which are known inhibitors of pre-rRNA synthesis and processing, respectively. The DNA gyrase inhibitor, ciprofloxacin, was found to act similarly to rifampicin; a decline in pre-rRNA was detectable within 15 minutes in ciprofloxacin susceptible bacteria. The invention provides assays for pre-rRNA, which provide insights into cellular metabolism as well as predictors of antibiotic susceptibility.

To address the need for antibiotic resistance data at the time of initial antibiotic selection, methods are described herein to analyze the antibiotic susceptibility of organisms in clinical specimens. The invention thus provides a method for detecting and identifying antibiotic susceptibility in a specimen containing, or suspected of containing, bacteria. In some embodiments, the method is used to guide diagnosis and treatment of a subject from whom the specimen containing bacteria has been obtained. For example, once the method has been employed to identify the antibiotic, or class of antibiotic, to which the specimen is susceptible, the method can further comprise administering the antibiotic to the subject.

Definitions

All scientific and technical terms used in this application have meanings commonly used in the art unless otherwise specified. As used in this application, the following words or phrases have the meanings specified.

As used herein, an "oligonucleotide probe" is an oligonucleotide having a nucleotide sequence sufficiently complementary to its target nucleic acid sequence to be able to form a detectable hybrid probe:target duplex under high stringency hybridization conditions. An oligonucleotide probe is an isolated chemical species and may include additional nucleotides outside of the targeted region as long as such nucleotides do not prevent hybridization under high stringency hybridization conditions. Non-complementary sequences, such as promoter sequences, restriction endonuclease recognition sites, or sequences that confer a desired secondary or tertiary structure such as a catalytic active site can be used to facilitate detection using the invented probes. An oligonucleotide probe optionally may be labeled with a detectable marker such as a radioisotope, a fluorescent moiety, a chemiluminescent moiety, an enzyme or a ligand, which can be used to detect or confirm probe hybridization to its target sequence. "Probe specificity" refers to the ability of a probe to distinguish between target and non-target sequences.

The term "nucleic acid", "oligonucleotide" or "polynucleotide" refers to a deoxyribo-nucleotide or ribonucleotide polymer in either single- or double-stranded form, and unless otherwise limited, encompasses known analogs of natural nucleotides that hybridize to nucleic acids in a manner similar to naturally-occurring nucleotides.

As used herein, a "detectable marker" or "label" is a molecule attached to, or synthesized as part of a nucleic acid probe. This molecule should be uniquely detectable and will allow the probe to be detected as a result. These detectable moieties are often radioisotopes, chemiluminescent molecules, enzymes, haptens, or even unique oligonucleotide sequences.

As used herein, a "hybrid" or a "duplex" is a complex formed between two single-stranded nucleic acid sequences by Watson-Crick base pairings or non-canonical base pairings between the complementary bases.

As used herein, "hybridization" is the process by which two complementary strands of nucleic acid combine to form a double-stranded structure ("hybrid" or "duplex"). "Stringency" is used to describe the temperature and solvent composition existing during hybridization and the subsequent processing steps. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. Stringency conditions are chosen to maximize the difference in stability between the hybrid formed with the target and the non-target nucleic acid. Exemplary stringency conditions are described herein below.

As used herein, "complementarity" is a property conferred by the base sequence of a single strand of DNA or RNA which may form a hybrid or double-stranded DNA:DNA, RNA:RNA or DNA:RNA through hydrogen bonding between Watson-Crick base pairs on the respective strands. Adenine (A) ordinarily complements thymine (T) or Uracil (U), while guanine (G) ordinarily complements cytosine (C). "Fully complementary", when describing a probe with respect to its target sequence, means that complementarity is present along the full length of the probe.

As used herein, "adjacent", in the context of nucleotide sequences and oligonucleotides, means immediately next to one another (end to end), such that two adjacent molecules do not overlap with one another and there is no gap between them. For example, two oligonucleotide probes hybridized to adjacent regions of a target nucleic acid molecule have no nucleotides of the target sequence (unpaired with either of the two probes) between them.

As used herein, the phrases "consist essentially of" or "consisting essentially of" mean that the oligonucleotide has a nucleotide sequence substantially similar to a specified nucleotide sequence. Any additions or deletions are non-material variations of the specified nucleotide sequence which do not prevent the oligonucleotide from having its claimed property, such as being able to preferentially hybridize under high stringency hybridization conditions to its target nucleic acid over non-target nucleic acids.

One skilled in the art will understand that substantially corresponding probes of the invention can vary from the referred-to sequence and still hybridize to the same target nucleic acid sequence. This variation from the nucleic acid may be stated in terms of a percentage of identical bases within the sequence or the percentage of perfectly complementary bases between the probe and its target sequence. Probes of the present invention substantially correspond to a nucleic acid sequence if these percentages are from 100% to 80% or from 0 base mismatches in a 10 nucleotide target sequence to 2 bases mismatched in a 10 nucleotide target sequence. In preferred embodiments, the percentage is from 100% to 85%. In more preferred embodiments, this percentage is from 90% to 100%; in other preferred embodiments, this percentage is from 95% to 100%.

By "sufficiently complementary" or "substantially complementary" is meant nucleic acids having a sufficient amount of contiguous complementary nucleotides to form, under high stringency hybridization conditions, a hybrid that is stable for detection.

By "preferentially hybridize" is meant that, under high stringency hybridization conditions, oligonucleotide probes can hybridize with their target nucleic acids to form stable probe:target hybrids (thereby indicating the presence of the target nucleic acids) without forming stable probe:non-target hybrids (that would indicate the presence of non-target nucleic acids from other organisms). Thus, the probe hybridizes to target nucleic acid to a sufficiently greater extent than to non-target nucleic acid to enable one skilled in the art to accurately detect the presence of the relevant bacteria and distinguish their presence from that of other organisms. Preferential hybridization can be measured using techniques known in the art and described herein.

As used herein, a "target nucleic acid sequence region" of a pathogen refers to a nucleic acid sequence present in the nucleic acid of an organism or a sequence complementary thereto, which is not present in the nucleic acids of other species. Nucleic acids having nucleotide sequences complementary to a target sequence may be generated by target amplification techniques such as polymerase chain reaction (PCR) or transcription mediated amplification.

As used herein, "room temperature" means about 20-25° C.

As used herein, "a" or "an" means at least one, unless clearly indicated otherwise.

Probes of the Invention

The invention provides oligonucleotide probes that are specific for bacterial rRNA. In a typical embodiment, the probes are fully complementary to the target sequence. Representative target sequences for probe hybridization with rRNA of indicated bacterial species are presented below:

*E. coli* (all enterobacteriaceae) target sequence:
(SEQ ID NO: 1)
AATGAACCGTGAGGCTT|AACCTTACAACGCCGAAGCTGTTTTGGCGGAT

TG;

*Pseudomonas aeruginosa* target sequence:
(SEQ ID NO: 2)
AATTGCCCGTGAGGCTT|GACCATATAACACCCAAACAATCTGACGATTG

T;

*Streptococcus pyogenes* target sequence:
(SEQ ID NO: 3)
AATAGCTCGAGGACTT|ATCCAAAAAGAAATATTGACAACGTTACGGATT

CTTG;

*Staphylococcus aureus* target sequence:
(SEQ ID NO: 4)
AATCGATCGAAGACTT|AATCAAAATAAATGTTTTGCGAAGCAAAATCAC

TT;

wherein | indicates the splice site between prRNA and mRNA.

Representative probe pairs directed to these target sequences include the following:

*E. coli* (all enterobacteriaceae) probes:
(SEQ ID NO: 5)
5'-AAGCCTCACGGTTCATT
and (SEQ ID NO: 6)
GGCGTTGTAAGGTT;

*Pseudomonas aeruginosa* probes:
(SEQ ID NO: 7)
5'-AAGCCTCACGGGCAATT
and (SEQ ID NO: 8)
GGTGTTATATGGTC;

*Streptococcus pyogenes* probes:
(SEQ ID NO: 9)
AAGTCCTCGAGCTATT
and (SEQ ID NO: 10)
ATTTCTTTTTGGAT;
and

*Staphylococcus aureus* probes
(SEQ ID NO: 11)
AAGTCTTCGATCGATT
and (SEQ ID NO: 12)
CATTTATTTTGATT.

Oligonucleotides may be prepared using any of a variety of techniques known in the art. Oligonucleotide probes of the invention include the sequences shown above and in Table 1 of the Example below, and equivalent sequences that exhibit essentially the same ability to form a detectable hybrid probe:target duplex under high stringency hybridization conditions. Oligonucleotide probes typically range in size from 10 to 50 nucleotides in length. Preferred probes are 10-35 nucleotides in length, with 10-25 nucleotides being optimal for some conditions. A variety of detectable labels are known in the art, including but not limited to, enzymatic, fluorescent, and radioisotope labels.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5 x Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

An advantage of the probes of the invention is their ability to hybridize to the target sequence with sufficient selectivity and strength at ambient temperature and without requiring the use of a denaturing agent. The probes of the invention can be used to detect species-specific targets at room temperature (or at body temperature), at native pH (7.0) in a 1M phosphate buffer. Accordingly, for the short (10-35 bases in length) probes of the invention, "highly stringent conditions" include hybridization and washes at 20° C. to 39° C. in 1M phosphate buffer, or other buffer containing an appropriate salt solution, at native pH (at or near 7.0).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

Any polynucleotide may be further modified to increase stability. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Nucleotide sequences can be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include probe generation vectors. In general, a vector will contain an origin of replication functional in at least one organism, convenient restriction endonuclease sites and one or more selectable markers. Other elements will depend upon the desired use, and will be apparent to those of ordinary skill in the art.

Methods of Detecting Antibiotic Susceptibility

The invention provides a method for determining whether a sample of bacteria of interest is susceptible to an antibiotic agent. In one embodiment, the method comprises contacting a probe that specifically binds to a target sequence of ribosomal RNA (rRNA), more specifically, pre-ribosomal ribonucleic acid (prRNA), of the bacteria of interest. In one embodiment, the target sequence comprises the junction, or splice site, between prRNA and mature ribosomal RNA (mRNA). The probe can be a single probe or a pair of probes, such as a capture probe and a detector probe. In one embodiment, the probe is a single probe that specifically hybridizes to target sequence spanning the prRNA-mRNA splice site. In another embodiment, the probe is a pair of probes that, collectively, specifically hybridize to target sequence spanning the prRNA-mRNA splice site. For example, each of the probes can hybridize to either side of the prRNA-mRNA splice site. The probe is contacted with the sample both in the presence and in the absence of the antibiotic agent. A reduced amount of probe hybridization in the presence of the antibiotic agent relative to the amount of probe hybridization in the absence of the antibiotic agent is indicative of the susceptibility of the sample to antibiotic.

In another embodiment, the method comprises contacting a specimen obtained from the sample of bacteria with an oligonucleotide probe or pair of probes in the absence of the agent. In one embodiment, the probe or pair of probes specifically hybridizes to a target sequence over the full length of the target sequence, wherein the target sequence consists of 25-35 contiguous nucleotides of bacterial ribosomal RNA (rRNA) spanning a splice site between a pre-ribosomal RNA (prRNA) tail and mature ribosomal RNA (mRNA). The method further comprises contacting a specimen obtained from the sample with the probe or pair of probes in the presence of the antibiotic agent; and detecting the relative amounts of probe hybridization to the target sequence in the specimens under the two contacting conditions. The sample is identified as susceptible to antibiotic treatment if the amount of probe hybridization to the target sequence in the presence of antibiotic is reduced by at least 80% relative to the amount of probe hybridization to the target sequence in the absence of antibiotic. In another embodiment, the amount of hybridization to the target sequence is reduced by 40%, 50%, 60%, 70%, 90%, or 95%, relative to the amount of probe hybridization to target sequence in the absence of antibiotic. Optionally, the method further comprises inoculating the specimen into a growth medium prior to the contacting steps.

The bacterial rRNA is typically 23S rRNA, or it can be 16S rRNA. The oligonucleotide probe or probes are typically each between about 10 to 50 nucleotides in length. In some embodiments, the probes are 12-30 nucleotides in length, while in others they range in length from 14-20 nucleotides in length. Optionally, the oligonucleotide probe is labeled with a detectable marker. Representative markers include, but are not limited to, a fluorescent label, a radioactive label, a luminescent label, an enzyme, biotin, thiol or a dye. The detecting step of the method can comprise an optical, electrochemical or immunological assay.

In one embodiment, the method further comprises lysing the bacteria under conditions that release rRNA from the bacteria prior to the contacting steps. Thus, the sample can be prepared with a lysis agent present. Preferably, the lysis agent is selected so as to release rRNA but without damaging the rRNA. The targeting of the prRNA-mRNA splice site means that the method can be performed without pre-treatment of the specimen to deplete prRNA prior to the contacting of probe with the sample, and without spliced prRNA tails interfering with the measurement. The ability to perform the method without such pre-treatment facilitates rapid processing of the susceptibility determination.

Antibiotic agents for susceptibility testing include, but are not limited to, Rifampicin, Chloramphenicol, aminoglycosides, quinolones, or beta-lactam antibiotics. In addition, novel or candidate antibiotic agents can be tested for efficacy using the methods described herein. The invention additionally provides a method of treating a subject having, or suspected of having, a bacterial infection. The method comprises determining the antibiotic susceptibility in a specimen obtained from the subject as described herein, and administering to the subject an antibiotic to which the specimen is susceptible.

A method for determining the antibiotic efficacy of a candidate antibiotic agent can comprise contacting a specimen obtained from the sample with an oligonucleotide probe or pair of probes in the absence of the agent, wherein the probe or pair of probes specifically hybridizes to a target sequence over the full length of the target sequence, wherein the target sequence comprises 25-35 contiguous nucleotides of bacterial ribosomal RNA (rRNA) spanning a splice site between pre-ribosomal RNA (prRNA) tail and mature ribosomal RNA (mrRNA), contacting a specimen obtained from the sample with the probe or pair of probes in the presence of the agent; and detecting the relative amounts of probe hybridization to the target sequence in the specimens. The agent is identified as effective if the amount of probe hybridization to the target sequence in the presence of the agent is reduced by at least 80% relative to the amount of probe hybridization to the target sequence in the absence of the agent.

Bacteria contained within the specimen can be lysed using one of the lysis preparations described herein. In one embodiment, the lysis preparation comprises the universal lysis buffer containing 1% Triton X-100, 0.1 M $KH_2PO_4$, 2 mM EDTA and 1 mg/ml lysozyme. Use of the universal lysis buffer obviates the need to use separate lysis buffer for gram-positive and gram-negative bacteria. In this embodiment, the time-consuming steps of bacterial RNA and/or DNA purification are not necessary, permitting direct application of a lysed urine sample to the capture probes, improving speed and efficiency of the assay. Accordingly, the method can be performed by first lysing a specimen of interest to release nucleic acid molecules of the pathogen.

Alternatively, the lysate can be prepared by contacting the specimen with a first lysis buffer comprising a non-denaturing detergent (e.g., Triton X-100) and lysozyme, or a second lysis buffer comprising NaOH. Typically, the Triton X-100 is used at 0.1%, lysozyme at 1 mg/ml, and NaOH at 1M. In another embodiment, the lysing comprises contacting the specimen with both buffers in series, e.g. with the second lysis buffer, either before or after contacting the specimen with the first lysis buffer. The contacting of the specimen with the buffer(s) typically occurs at room temperature. Typically, the specimen is in contact with the lysis buffer for a total of about 10 minutes. Where a first and second lysis buffer is used, the contact with each buffer is typically about 5 minutes. Those skilled in the art are aware that the time and temperature under which the contact with lysis buffer occurs can be varied (e.g. higher temperatures will accelerate the lysis) and also optimized for a particular specimen, target pathogen and other assay conditions.

The method comprises contacting a specimen with one or more detector probes of the invention under conditions permitting hybridization of target nucleic acid molecules of pathogens (e.g., bacteria) present in the specimen with the detector probes, resulting in hybridized target nucleic acid molecules. One or more hybridized target probes are brought into contact with one or more capture probes, under conditions permitting hybridization of capture probes with target nucleic acid molecules.

Accordingly, the target nucleic acid ultimately hybridizes with both capture probe(s) and detector probe(s). Although these two hybridization steps can be performed in any order, in one embodiment, detector probe hybridizes with the target nucleic acid first, after which the hybridized material is brought into contact with an immobilized capture probe. Following a wash, the dectector:target:capture combination is immobilized on a surface to which the capture probe has been bound. Detection of probe bound to target nucleic acid is indicative of presence of pathogen.

For use with an electrochemical sensor, such as the sensor array available from GeneFluidics, Inc. (Monterey Park, Calif.), the method comprises detection of current associated with binding of probe to target. In one embodiment illustrated in the example below, the capture probe is labeled with biotin and immobilized onto a surface treated with streptavidin. The detector probe in this example is tagged with fluorescein, providing an antigen to which a horse radish peroxidase-labeled antibody binds. This peroxidase, in the presence of its substrate (typically, hydrogen peroxide and tetramethylbenzidine), catalyzes a well-characterized redox reaction and generates a measurable electroreduction current under a fixed voltage potential, thereby providing an electrochemical signal to detect presence of the target nucleic acid. Those skilled in the art are aware of alternative labels and enzymes that can be used in an electrochemical assay.

Preferably, the method for detecting antibiotic resistance is performed after first identifying and quantifying the pathogen of interest. The method of detecting the presence of a pathogen set forth in U.S. Pat. No. 7,763,426 can be used to identify the pathogen. Identification of the pathogen guides the selection of antibiotic to be tested for resistance. Quantitation of the pathogen guides the selection of an appropriate ratio of antibiotic to pathogen for subsequent testing. The method is then carried out by inoculation of the pathogen-containing specimen into a growth medium. The inoculation is performed at a dilution determined by the results of the quantitation. This inoculation is preferably done in both the presence and absence of antibiotic. The presence or amount of pathogen is then determined, typically by comparing the specimens inoculated in the presence and in the absence of antibiotic. A greater pathogen amount in the presence of antibiotic is indicative of resistance to the antibiotic. The comparison is typically based on comparing the amount of labeled oligonucleotide (detector probe) complexed with the substrate for inoculations into growth medium in the presence and absence of antibiotic.

Methods of Monitoring Bacterial Growth Rate

The invention also provides a method for monitoring the growth rate of a bacterial culture. The method comprises contacting a specimen obtained from the culture with a probe or pair of probes that specifically hybridizes to a target sequence over the full length of the target sequence, wherein the target sequence comprises 25-35 contiguous nucleotides of bacterial ribosomal RNA (rRNA) spanning a splice site between pre-ribosomal RNA (prRNA) tail and mature ribosomal RNA (mrRNA). The method further comprises detecting the amount of probe hybridization to the target sequence in the specimen relative to an earlier time point; and/or relative to a control that either lacks or includes a growth medium component to be tested. The culture is identified as growing, or in a log phase of growth, if the amount of probe hybridization to the target sequence at the subsequent time point is increasing relative to the amount of probe hybridization to the target sequence at the earlier time point.

Kits and Devices

The invention additionally provides a device for detecting pre-rRNA in a bacterial sample. The device, in one embodiment, comprises an oligonucleotide probe immobilized on a solid support, wherein the oligonucleotide probe is between about 10 to 50 nucleotides in length and is capable of selectively hybridizing to a target sequence over the full length of the target sequence. The target sequence typically comprises 25-35 contiguous nucleotides of bacterial ribosomal RNA (rRNA) spanning a splice site between pre-ribosomal RNA (prRNA) tail and mature ribosomal RNA (mrRNA). The solid support is typically an electrode or a membrane. Also contemplated is an ELISA well, or optical surface.

The invention further comprises a kit that can be used in practising the methods described herein. The kit can comprise an oligonucleotide probe or a pair of oligonucleotide probes selected from those described herein. The probes can optionally be labelled with a detectable marker. The kit can further comprise one or more containers for housing the probe(s) and other reagents for use with the method. The invention additionally provides an assay kit for use in carrying out the method of the invention. The kit comprises one or more of the probes described herein, and, optionally, a container or substrate. In one embodiment, the kit comprises a substrate to which one or more capture probes of the invention are bound or otherwise immobilized. Optionally, the kit further comprises a container and one or more detector probes corresponding to the capture probes. In one embodiment, the substrate is an electrochemical sensor array.

EXAMPLES

The following examples are presented to illustrate the present invention and to assist one of ordinary skill in making and using the same. The examples are not intended in any way to otherwise limit the scope of the invention.

Example 1

Rapid Antimicrobial Susceptibility Testing by Sensitive Detection of Precursor rRNA Using a Novel Electrochemical Biosensing Platform Ribosomal RNA is an excellent target molecule for pathogen detection systems because of its abundance in the bacterial cell and because of the accessibility of species-specific signature sequences to probe hybridization (6). When combined with sensitive surface chemistry methods to minimize nonspecific background signals, such rRNA probe hybridization sensors are able to detect as few as 100 bacteria per ml (2, 8, 17). Estimations of bacterial density are possible because, within the dynamic range of the assay, there is a log-log correlation between the concentration of target rRNA molecules in the bacterial lysate and the amperometric current amplitude generated by the electrochemical sensor assay (10, 12). The accuracy of bacterial quantitation methods based on rRNA detection is mitigated by variations in the number of rRNA molecules per cell depending on the cell type and bacterial growth phase. In *E. coli*, the rRNA copy number per cell has been estimated to vary from as high as 72,000 during log phase to less than 6,800 during stationary phase (1).

Electrochemical sensors have the potential to rapidly determine antibiotic susceptibility by monitoring the phenotypic response of bacteria to antibiotics. Cellular pre-rRNA levels would be expected to fall as antibiotics shift the cellular metabolism of antibiotic-susceptible bacteria from log phase to stationary phase. The size of the pre-rRNA pool in the cell is determined by the synthesis and degradation rates, which are directly or indirectly affected by antibiotics (3). For this reason, we developed and validated an electrochemical assay for pre-rRNA determination. By calibrating sensor signal intensities with an internal standard, and correlating these signals with bacterial density, we were able to estimate the number of rRNA and pre-rRNA copies per cell. Our studies provide new insight into the kinetics of rRNA and pre-rRNA levels during bacterial growth phases, and in response to certain antibiotics. Of interest, we determined that pre-rRNA and/or rRNA levels rapidly respond to the quinolone antibiotic, ciprofloxacin, and the aminoglycoside antibiotic, gentamicin, in susceptible *E. coli*.

Materials & Methods

Bacterial Strains and Media. *E. coli* clinical urine isolate EC103 (Amp$^R$) was obtained from the University of California-Los Angeles (UCLA) Clinical Microbiology Laboratory with approval from the UCLA and Veterans' Affair Institutional Review Boards and appropriate Health Insurance Portability and Accountability Act exemptions. EC103 was inoculated into Mueller Hinton (MH) broth with 12% glycerol (Becton Dickinson, Sparks, Md.) and stored at −80° C. EC103 was cultured overnight in MH broth with 64 µg/mlampicillin (Sigma, St. Louis, Mo.). EC103 was plated on Luria Broth (LB) agar (MOBIO Laboratories Inc., Carlsbad, Calif.) for counting colony-forming units (CFUs).

EC103 Growth and Target Copy Number Experiments. Overnight cultures of EC103 were prepared by adding 5 µl of EC103 glycerol stock to 5 ml of MH broth with ampicillin and incubated at 37° C. overnight with shaking. The following day, the EC103 culture was diluted by adding 10 µl of the overnight culture to 100 ml of prewarmed and preshaken MH broth in a 500 ml flask, followed by incubation at 37° C. with shaking at 250 rpm. Every 30 min, including at 0 min and the overnight culture itself, a 1 ml sample was taken for $OD_{600}$ measurement and 10-fold serial dilutions (100 µl into 900 µl) were performed in room temperature MH broth. Cell density was determined by plating serial dilutions in triplicate. At each time point, culture samples were transferred to an ice water bath or centrifuged immediately at 4° C. for 3 min at 14,000 rpm. The supernatants were then removed by aspiration, flash frozen in a dry ice-ethanol bath and stored at −80° C.

In certain growth experiments, one culture was spiked with one of the following antibiotics at either 150 or 210 minutes: 25 µg/ml Rifampicin (Sigma, St. Louis, Mo.), 25 µg/ml Chloramphenicol (Sigma, St. Louis, Mo.), 4 µg/ml Ciprofloxacin (Sigma, St. Louis, Mo.) or 16 µg/ml Gentamicin (Sigma, St. Louis, Mo.). After addition of antibiotics at 150 minutes, samples were collected every 15 min instead of every 30 min.

For experiments comparing pre-ribosomal probe sensitivity and specificity, culture samples were taken from the overnight culture and the EC103 culture at log phase ($OD_{600}$=0.1) and centrifuged immediately at 4° C. for 5 min at 14,000 rpm. Supernatants were removed by aspiration. The pellets were flash frozen in a dry ice-ethanol bath and stored at −80° C.

Electrochemical detection. Electrochemical detection of bacterial rRNA and pre-rRNA was performed as previously described for biotinylated (12) and thiolated capture probes (2, 8) immobilized on photolithographically prepared Au electrode arrays, with modifications.

The sensor response was evaluated with a sandwich-type hybridization assay, using fluorescein (FITC) as a tracer in the detection probe and anti-FITC-horseradish peroxidase (HRP) as the reporter molecule. 3,3'5,5'-tetramethylbenzidine (TMB)-$H_2O_2$ was the selected substrate for the electrochemical measurement of the activity of the captured HRP reporter. All synthetic oligonucleotides used were purchased from Eurofins MWG Operon and are listed in Table 1. For thiolated capture probes, disposable 16-sensor bare Au electrode arrays were obtained from GeneFluidics (Irwindale, Calif.). Each sensor of the array consisted of a 2.5 mm diameter central working electrode, surrounded by an Au counter electrode and an Au pseudo-reference electrode. The sensor chip was driven by a computer-controlled Helios multichannel electrochemical workstation (GeneFluidics, Irwindale, Calif.). Washing steps were carried out after each application of reagents by applying a stream of deionized $H_2O$ to the sensor surface for approximately 2-3 sec followed by 5 sec of drying under a stream of nitrogen. Prior to addition of the first reagent, the bare gold chips were dried as described above. To functionalize the working sensor surface, a fresh mixture of 0.05 µM thiolated capture probe and 300 µM 1,6-hexanedithiol (96%, Sigma, St. Louis, Mo.) was prepared in 10 mM Tris-HCl, 1 mM EDTA and 0.3 M NaCl (pH 8.0) and allowed to stand at room temperature for 10 min. Aliquots of 6 µl of this mixture were cast over each Au working electrode in the 16-sensor array and incubated overnight at 4° C. in a humidified chamber. Unless otherwise stated, all subsequent steps were performed at room temperature. The following day, the mixed monolayer-modified Au sensors were subsequently treated with 6 ul of 1 mM 6-Mercapto-1-hexanol (97%, Sigma, St. Louis, Mo.) in 10 mM Tris-HCl, 1 mM EDTA and 0.3 M NaCl (pH 8.0) for 50 min to obtain the ternary monolayer interface.

For biotinylated capture probes, 16-sensor Au electrode arrays precapped with a binary SAM consisting of mercaptohexanol and mercaptoundecanoic acid in a 5:1 ratio were obtained from GeneFluidics (Irwindale, Calif.). Washing steps were carried out after each application of reagents by applying a stream of deionized $H_2O$ to the sensor surface for approximately 2-3 sec followed by 5 sec of drying under a stream of nitrogen. To functionalize the sensor surface, the carboxylic terminal groups of the binary SAM were converted to amine-reactive esters by applying 4 µl of a NHS/EDC (50 mM N-hydroxysuccinimide, 200 mM N-3-dimethylaminopropyl-N-ethylcarbodiimide, Sigma, St. Louis, Mo.) solution in deionized $H_2O$ to the working electrode for 10 min. Activated sensors were incubated for 10 min with 4 µl of EZ-Link Amine-$PEG_2$-Biotin (Pierce, Rockford, Ill.) at a concentration of 5 mg/ml in 50 mM sodium acetate, pH 5. 30 µl of 1M ethanolamine, pH 8.5 (Sigma, St. Louis, Mo.) was applied to all three electrodes for 10 min in order to block the remaining reactive groups of the activated monolayer. Biotinylated sensors were incubated in 4 µl of 0.5 mg/ml of streptavidin (Pierce) in RNase-free $H_2O$ (Cat. No. 821739, MP Biomedicals, Aurora, Ohio) for 10 min. Streptavidin-coated sensors were incubated with biotinylated capture probes (4 µl, 1 µM in 1 M phosphate buffer, pH 7.2) for 30 min. Electrodes were blocked for 10 min with 4 µl of 0.05% polyethylene glycol 3350 (PEG, Sigma, St. Louis, Mo.) in 1M phosphate buffer, pH 7.2. All these incubation steps were performed in a glass petri dish.

For both capture probe types, lysis of bacterial cells was performed by resuspending the appropriate pellet in 10 µL of 1M NaOH and incubating at room temperature for 5 min. Bacterial lysates were neutralized by addition of 50 µl of 0.25 µM fluorescein (FITC)-modified detector probe in 1M Phosphate Buffer pH 7.2 with 2.5% Bovine Serum Albumin (BSA) (Sigma, St. Louis, Mo.) and allowed to react for 10 min for homogeneous hybridization. Aliquots (4 µl) of this raw bacterial lysate target solution were cast onto each capture probe-modified sensor and incubated for 15 min. After washing and drying the array, 4 µl of a 0.5 U/ml anti-FITC horseradish peroxidase (HRP) Fab fragments (Roche, diluted in 0.5% casein in 1M phosphate buffered saline, pH 7.2) solution were deposited on each of the working electrodes for 15 min. After washing and drying, a prefabricated plastic 16-well manifold (GeneFluidics, Irwindale, Calif.) was bonded to the sensor array. The sensor array was put into the chip reader and 50 µl of the $TMB-H_2O_2$ solution (Enhanced K-Blue TMB Substrate, Neogen, Lexington, Ky.) was placed on each of the sensors in the array, covering the three-electrode area. Chronoamperometric measurements were immediately and simultaneously taken for all 16 sensors by stepping the potential to −200 mV (vs the quasi Au reference electrode) and sampling the current at 60 s. For each array, negative control (NC) sensors were tested including the capture probe, FITC-detector probe, and the buffer (2.5% BSA in 1 M phosphate buffer, pH 7.2) instead of bacterial lysate solution. Positive controls (PC) were included in all sensor arrays and consisted of a synthetic target oligonucleotide for either the mature rRNA or Pre23S 3'Jxn pre-rRNA probe pairs at 1 nM with the corresponding detector probe (see Table 1).

Including the synthetic target molecule served to normalize the electrochemical signal intensity and determine the ribosomal and pre-ribosomal target molecule concentration because there is a linear log/log correlation between the concentration of the analyte and the electrochemical signal. The relation between the electrochemical signal generated and the number of synthetic target molecules tested were used to convert the electrochemical signal from samples at each time point into a number of target molecules per volume tested (concentration). This was then combined with the CFU/ml values determined by plating for each time point to generate target molecule number per CFU measurements.

Cryo-electron microscopy (cryo-EM) of frozen-hydrated E. coli. E. coli cultures (5 ul) were deposited onto a freshly glow discharged holey carbon grid, then blotted, and rapidly frozen in liquid ethane. The frozen-hydrated specimens were imaged at −170° C. using a Polara G2 electron microscope (FEI Company, Hillsboro, Oreg.) equipped with a field emission gun and a 4K×4K charge-coupled device (CCD; TVIPS, GMBH, Germany). The microscope was operated at 300 kV, and cryo-EM images were recorded at the magnification of 4,700×(3.76 nm/pixel) and 31,000×(0.57 nm/pixel), respectively. 9-14 cells were selected at random for length and width measurements at different times after inoculation.

Results

Figure 2:
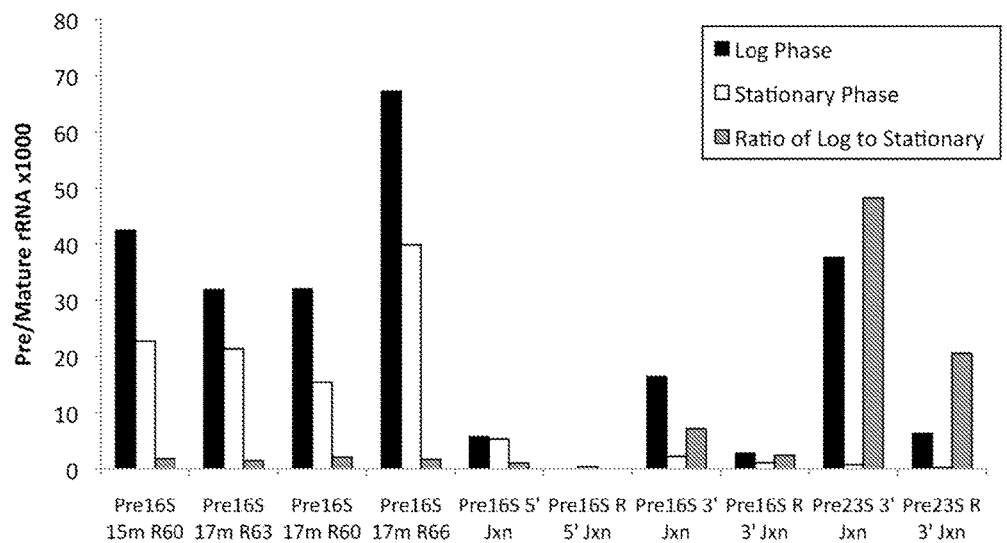
FIG. 2. Comparison of pre-rRNA probe pairs. Probe pairs were tested for detection of *E. coli* in the log and stationary phases of growth. Log and stationary phase cells are expected to have high and low levels of pre-rRNA, respectively, yielding a high signal ratio for log vs. stationary phase cells. Probe pairs for 16S pre-rRNA had good sensitivity for log phase cells but the signal ratio for log vs. stationary phase cells was low. Some probe pairs targeting the splice sites at the termini of mature 16S and 23S rRNA had higher signal ratios for log vs. stationary phase cells. The probe pair targeting the splice site at the 3' terminus of 23S rRNA had the best combination of sensitivity and high signal ratio of log vs. stationary phase cells.

Development of Capture & Detector Probes for Pre-rRNA. Probe pairs were developed for pre-rRNA tails that are removed during rRNA processing (FIG. 1). Initially, probe pairs of various lengths were designed for a region in the 5' tail of 16S pre-rRNA predicted to be accessible for probe binding because it was relatively free of secondary structure. As shown in FIG. 2, some of these probe pairs demonstrated good sensitivity (high signal-to-noise ratio) for E. coli samples obtained during the log phase of growth. However, these 16S pre-rRNA probes generated unexpectedly low ratios of log phase to stationary phase signals when E. coli in different growth phases were tested (FIG. 2). These results indicated that such probes were not reliable markers for intact pre-rRNA molecules.

Subsequently, probe pairs were designed to hybridize with splice sites between the pre-rRNA tails and mature rRNA so that the target sequences would only be present in intact pre-rRNA (FIG. 1). These target sequences are digested into two pieces during processing of pre-rRNA into mature rRNA such that after digestion, neither piece of the target sequence would bind the probe sufficiently well to generate a signal. Probe pairs were tested for binding to the 5' and 3' splice sites of 16S rRNA and the 3' splice site of 23S rRNA. Probe pairs in both the capture-detector and detector-capture orientations were tested. As shown in FIG. 2, pre-rRNA probe pairs targeting the splice sites resulted in higher ratios of log to stationary phase signals. These results are consistent with those of Cangelosi et al (3) who used a pre-rRNA sandwich hybridization assay in which their capture probe bound to the pre-rRNA tail and their detector probe bound to the mature rRNA region providing specificity for intact pre-rRNA. One of the two probe pairs for the 3' splice site of 23S rRNA produced a high signal with a relatively high signal ratio for log phase compared to stationary phase cells. This capture (Pre23S 14m 3'JxnC) and detector (Pre23S 17m 3'JxnD) probe pair was selected for subsequent measurements of pre-rRNA.

For mature rRNA determination capture and FITC-detector probes specified in Table 1 were used.

Growth Phase Comparison of Mature rRNA vs. Pre-rRNA. We compared signals for mature rRNA vs. pre-rRNA for an overnight culture of E. coli before and after inoculation into fresh MH medium. Target rRNA and pre-rRNA concentrations were estimated by including known concentrations of synthetic artificial target oligonucleotides as internal calibration controls on each electrochemical sensor chip. These synthetic target oligonucleotides functioned by hybridizing with both the capture and detector probes. Copies per cell were calculated from the concentrations of the rRNA target number and the number of cells in the bacterial lysate. We found that variability in pre-rRNA and rRNA measurements could be reduced by chilling samples in an ice bath and centrifugation in a centrifuge refrigerated at 4° C. On the other hand, the cells were sensitive to cold shock particularly during the lag and early log phases of growth. For this reason, accurate plate counts were obtained by dilution of the culture in room temperature medium rather than cold medium.

Figures 3A, 3B:
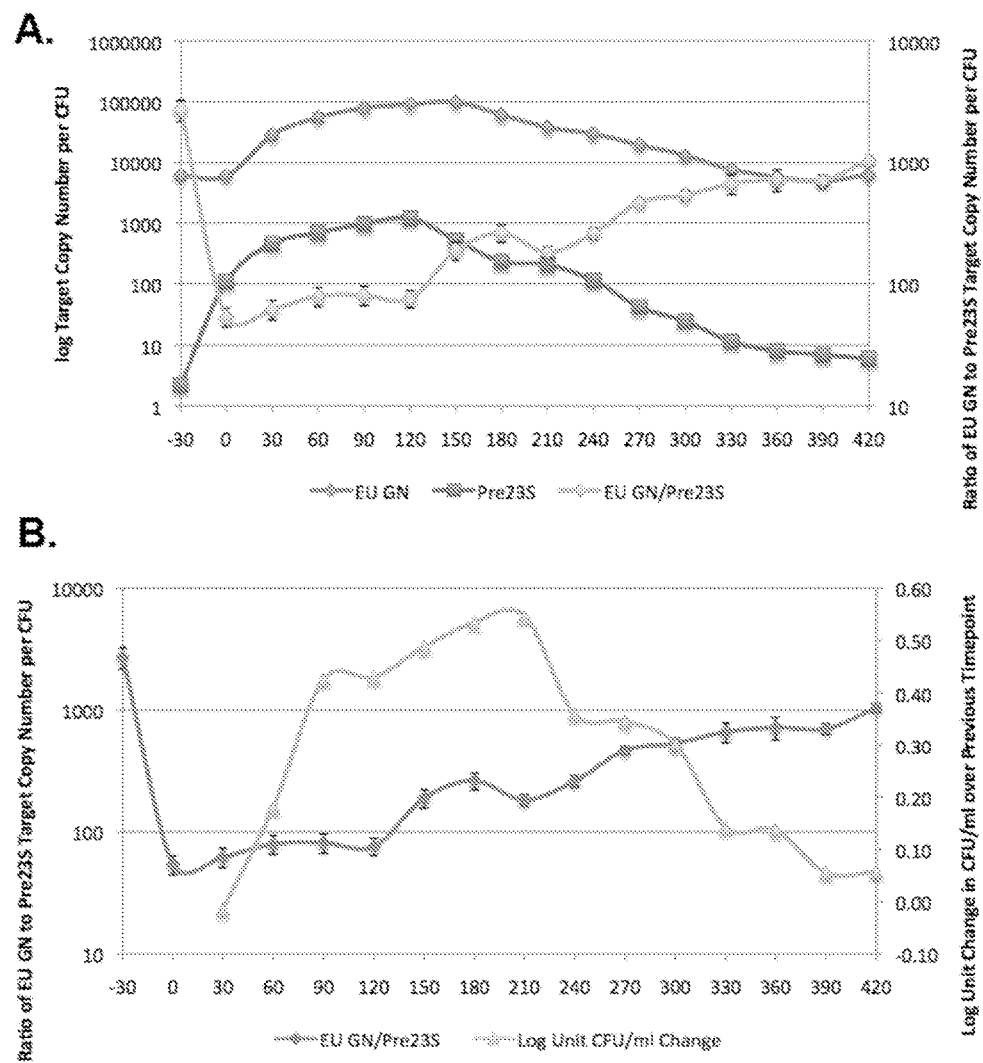
FIGS. 3A-3B. Variations in pre-rRNA and rRNA levels during *E. coli* growth.

Immediately after inoculation of overnight culture into fresh growth medium (Table 2, time 0), there was a 55-fold increase in pre-rRNA from 2 copies per cell to 110 copies per cell, indicating a dramatic induction of rRNA synthesis. At that point, the ratio of mature rRNA to pre-rRNA reached a nadir of 54:1. As shown in FIG. 3, pre-rRNA levels continued to increase during the first two hours of incubation, peaking at 120 min after incubation at 1,200 copies per cell. As pre-rRNA was converted to mature rRNA, copies of mature rRNA peaked at >98,000 copies per cell at 150 min after inoculation. Despite a gradual drop in both mature rRNA and pre-rRNA thereafter, growth rate peaked at 210 min at 1.1 log unit increase in cellular concentration per hour, which equals a doubling time of 16.5 min. During the later phases of growth, pre-rRNA copy numbers dropped more quickly than mature rRNA copy numbers, eventually leading to an increase in the ratio of mature rRNA to pre-rRNA to >1000:1.

Figures 4A, 4B:
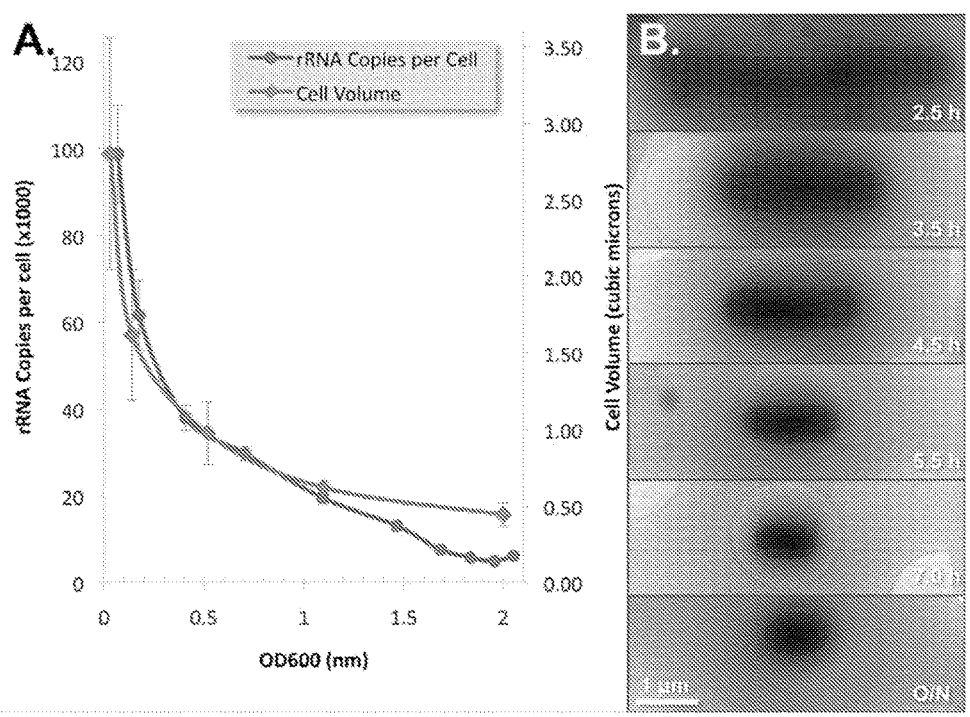
FIGS. 4A-4B. *E. coli* cell volume vs. rRNA copy number during different growth phases.

As shown in FIG. 4A, there was a good correlation between cell volume and rRNA copies per cell during log and late log phases of growth, indicating a relatively constant rRNA density in the cytoplasm. This correlation was lost at cell densities above $OD_{600\,nm}=1.0$, at which point the cell volume stabilized while the rRNA copy number continued to fall. Cryo-electron microscopy was performed to measure E. coli cell volumes at different growth phases. As shown in FIG. 4B, E. coli cells became progressively shorter and thinner as cells went from log phase to stationary phase. The peak average cell size was 2.8 µm$^3$ (4.87 µm long×0.85 µm wide) and the smallest average cell size was 0.45 µm$^3$ (1.35 µm long×0.65 wide).

Figure 5A:
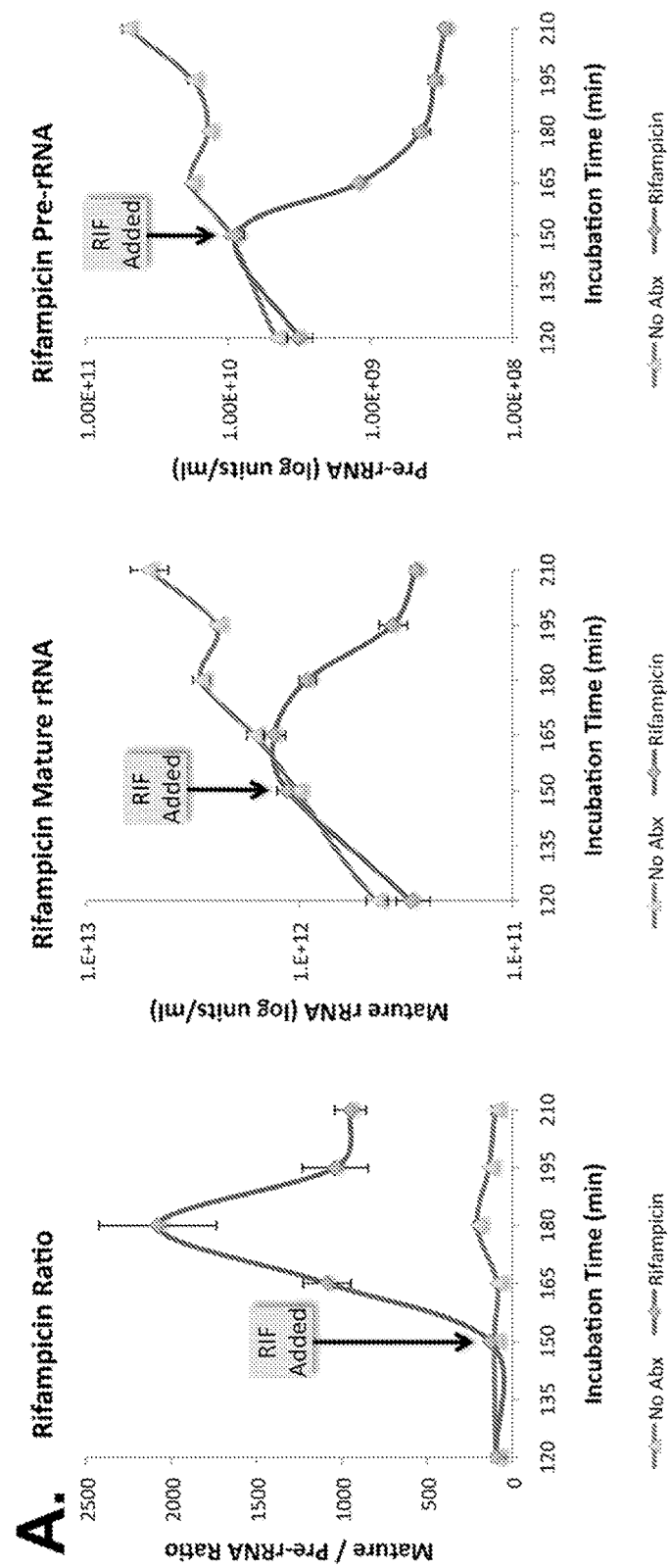
FIGS. 5A-5D. Response of mature rRNA and pre-rRNA to antibiotics. Antibiotics have differential effects on rRNA and pre-rRNA. Rifampicin (FIG. 5A) and ciprofloxacin (FIG. 5C) selectively inhibited transcription of new pre-rRNA, while addition of chloramphenicol (FIG. 5B) and gentamicin (FIG. 5D) resulted in a selective decrease in mature rRNA. Errors bars estimated the standard deviation.
Figure 5B:
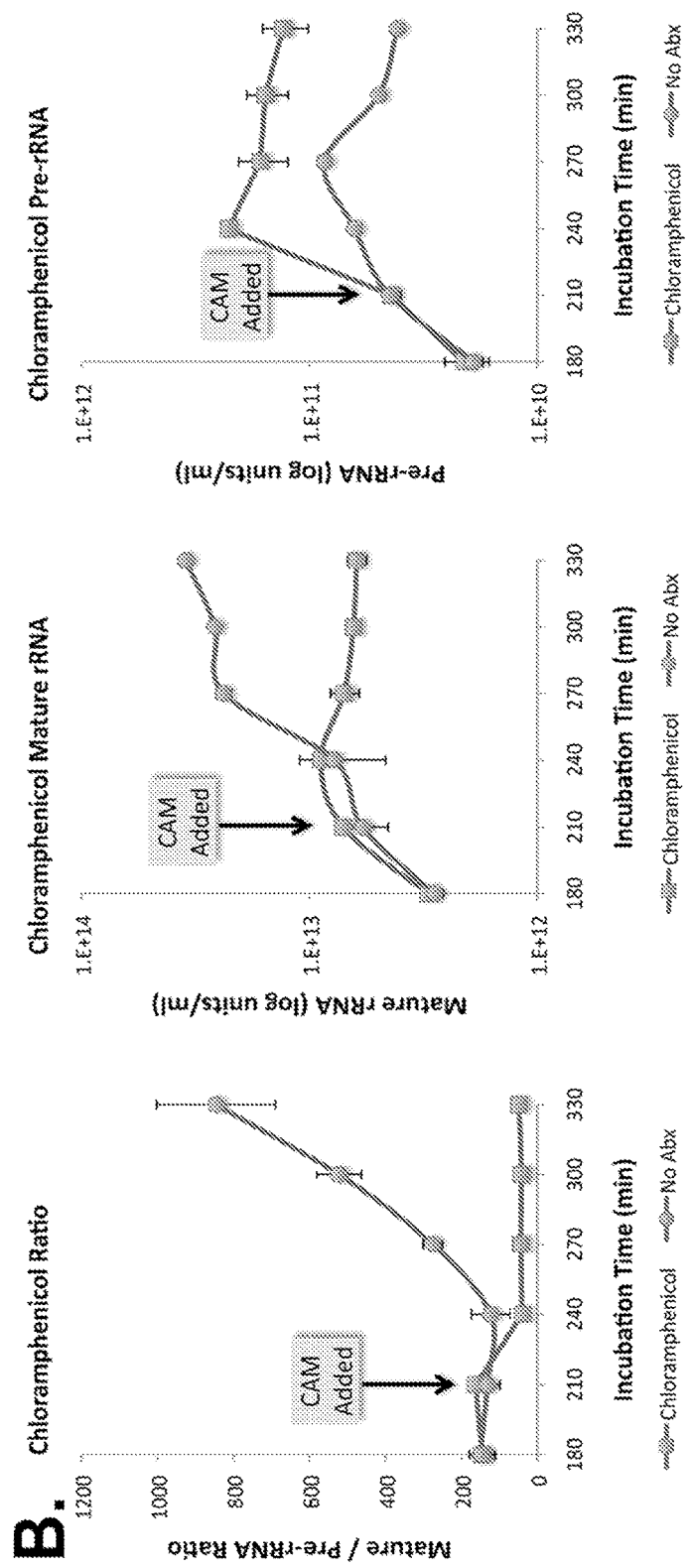
Figure 5C:
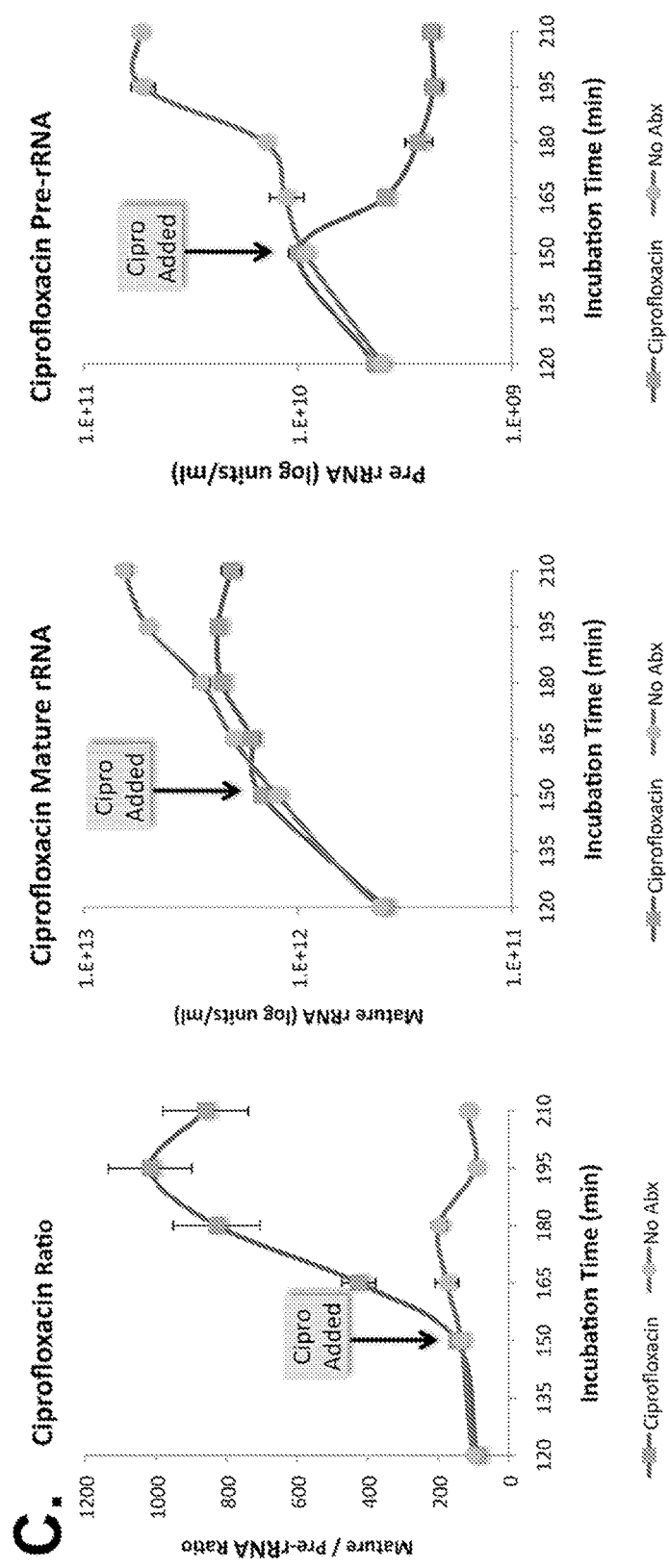
Figure 5D:
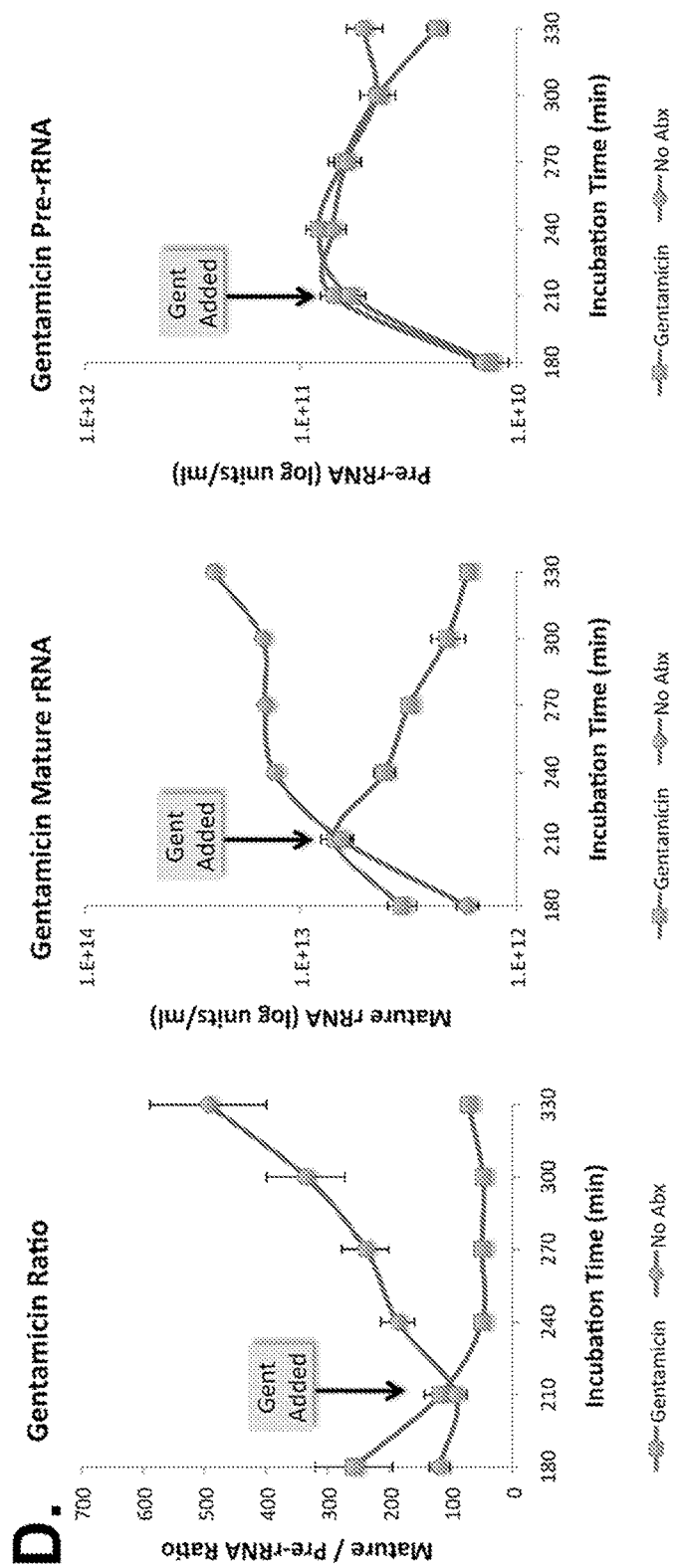
Figure 6A:
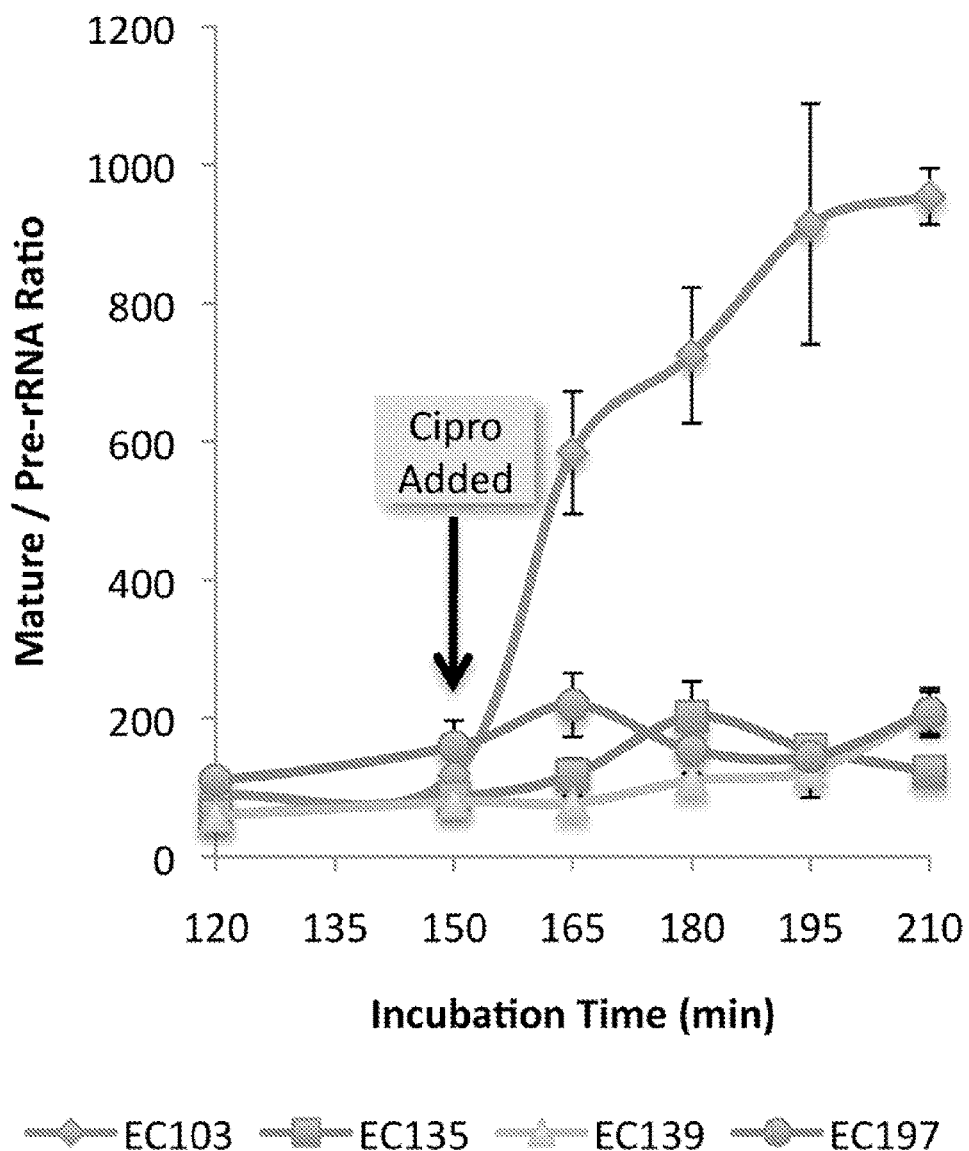
FIGS. 6A-6C. Comparison of ciprofloxacin susceptible and resistant *E. coli* strains. rRNA and pre-rRNA were measured in cultures of an *E. coli* clinical isolate susceptible to ciprofloxacin (EC103) and three ciprofloxacin resistant isolates (EC135, EC139, and EC197). The amount of pre-rRNA in strain EC103 was significantly lower than that of the ciprofloxacin resistant isolates within 15 min after addition of the antibiotic. Errors bars estimated the standard deviation.
Figure 6B:
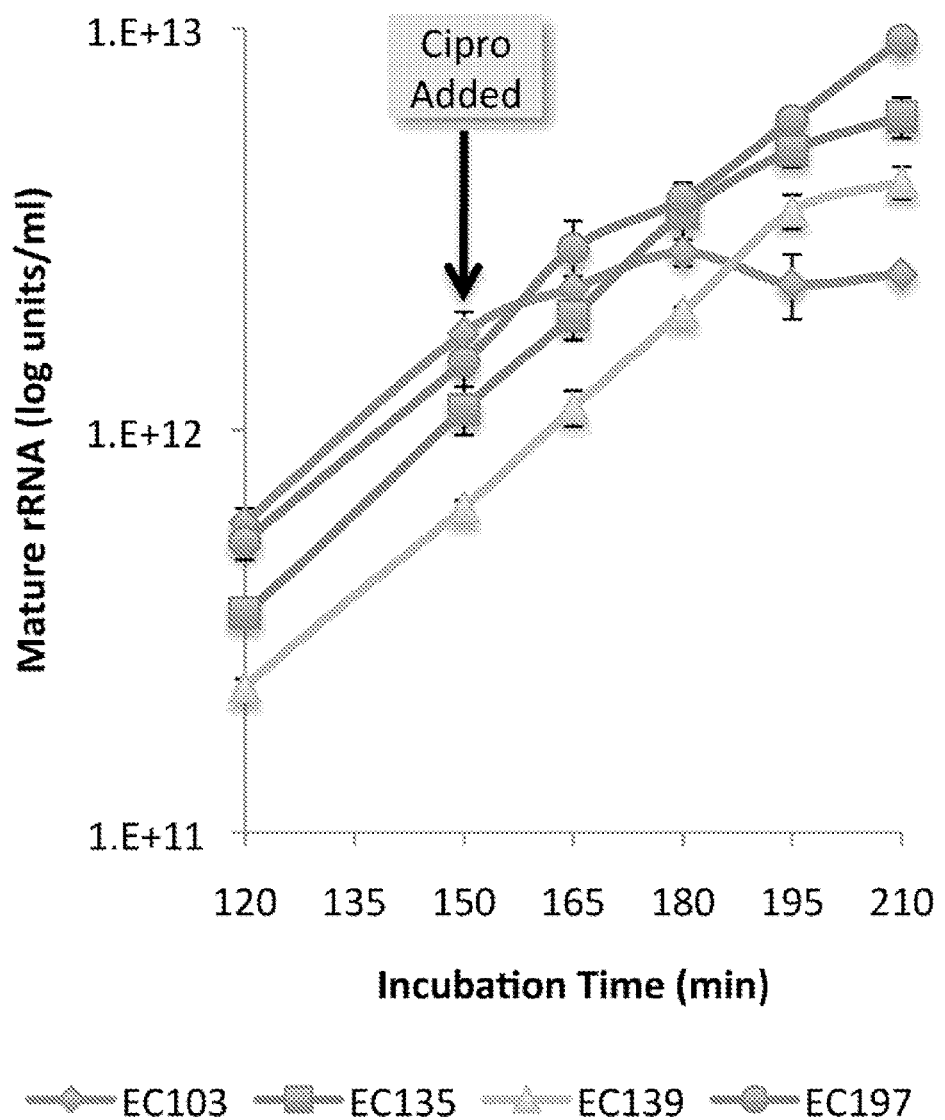
Figure 6C:
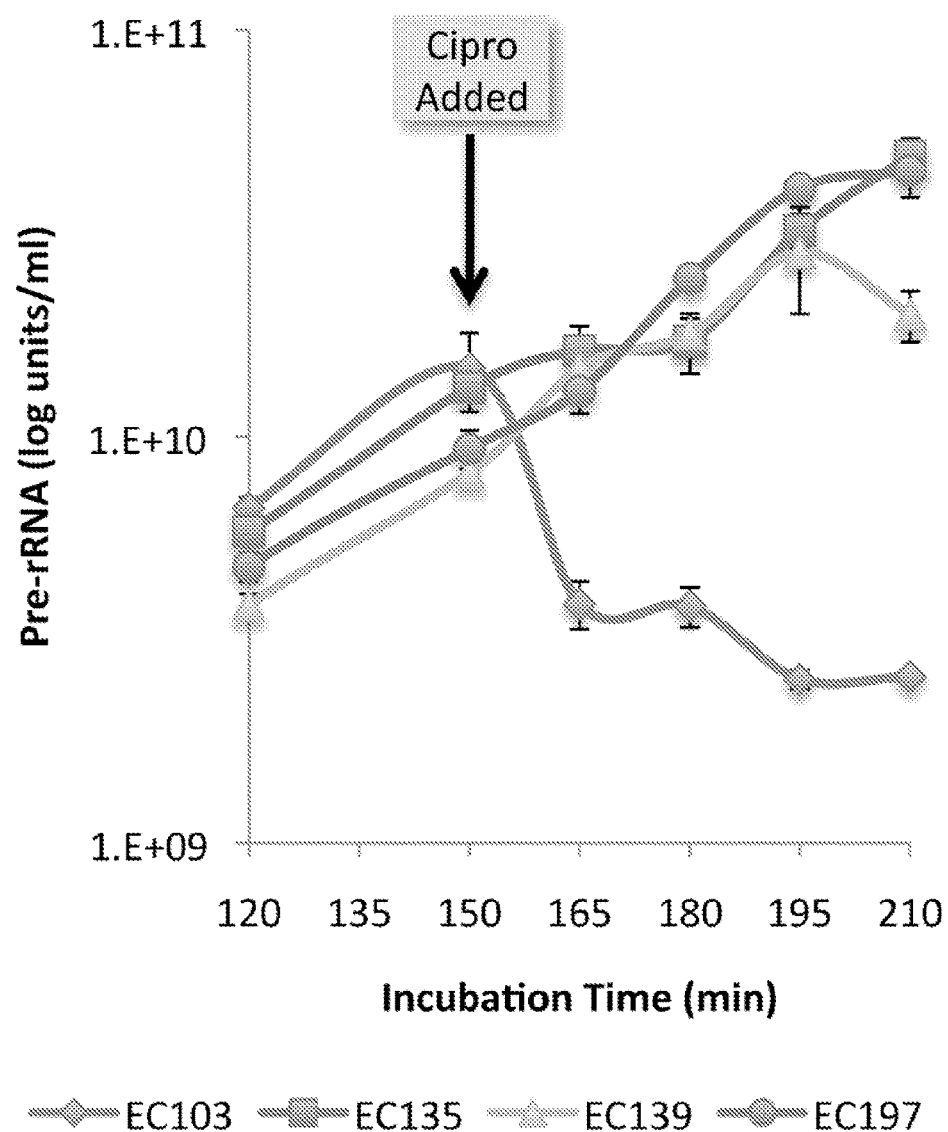

Effects of antibiotics on mature rRNA and pre-rRNA levels. To confirm that the pre-rRNA capture and detector probes were selective for the desired target, we examined the effects of rifampicin and chloramphenicol on pre-rRNA levels relative to mature rRNA. Consistent with a previous report (3), addition of rifampicin caused a selective drop in pre-rRNA, while chloramphenicol caused a selective increase in pre-rRNA (FIGS. 5A & 5B). The effects of ciprofloxacin and gentamicin on pre-rRNA and mature rRNA levels were also examined. As shown in FIG. 5C, ciprofloxacin had an effect similar to that of rifampicin; pre-rRNA levels dropped significantly within 15 min while mature rRNA remained at control levels until 45 min after addition of the antibiotic. In contrast, there was no effect of this antibiotic on the pre-rRNA levels of ciprofloxacin-resistant organisms (FIG. 6). Addition of gentamicin resulted in a decrease in mature rRNA without affecting the level of pre-rRNA (FIG. 5D).

TABLE 1

DNA oligonucleotides used in this study

| Probe Name[1] | Sequence[2] | SEQ ID NO: |
|---|---|---|
| Pre16S 15m 48D | 5'-TTTTTCGTCTTGCGA-F | 13 |
| Pre16S 15m 63C | 5'-B-GAGACTTGGTATTCA | 14 |
| Pre16S 15m R63D | 5'-F-GAGACTTGGTATTCA | 15 |
| Pre16S 15m R48C | 5'-TTTTTCGTCTTGCGA-B | 16 |
| Pre16S 17m R63D | 5'-F-TTGAGACTTGGTATTCA | 17 |
| Pre16S 17m R46C | 5'-TTTTTCGTCTTGCGACG-B | 18 |
| Pre16S 19m R63D | 5'-F-TCTTGAGACTTGGTATTCA | 19 |
| Pre16S 19m R44C | 5'-TTTTTCGTCTTGCGACGTT-B | 20 |
| Pre16S 21m R63D | 5'-F-ACTCTTGAGACTTGGTATTCA | 21 |
| Pre16S 21m R42C | 5'-TTTTTCGTCTTGCGACGTTAA-B | 22 |
| Pre16S 17m R60D | 5'-F-AGACTTGGTATTCATTT | 23 |
| Pre16S 17m R43C | 5'-TTCGTCTTGCGACGTTA-B | 24 |
| Pre16S 19m R60D | 5'-F-TGAGACTTGGTATTCATTT | 25 |

TABLE 1-continued

DNA oligonucleotides used in this study

| Probe Name[1] | Sequence[2] | SEQ ID NO: |
|---|---|---|
| Pre16S 19m R41C | 5'-TTCGTCTTGCGACGTTAAG-B | 26 |
| Pre16S 21m R6OD | 5'-F-CTTGAGACTTGGTATTCATTT | 27 |
| Pre16S 21m R39C | 5'-TTCGTCTTGCGACGTTAAGAA-B | 28 |
| Pre16S 17m R66D | 5'-F-CTCTTGAGACTTGGTAT | 29 |
| Pre16S 17m R49C | 5'-TCATTTTTCGTCTTGCG-B | 30 |
| Pre16S 19m R66D | 5'-F-CACTCTTGAGACTTGGTAT | 31 |
| Pre16S 19m R47C | 5'-TCATTTTTCGTCTTGCGAC-B | 32 |
| Pre16S 21m R66D | 5'-F-TTCACTCTTGAGACTTGGTAT | 33 |
| Pre16S 21m R45C | 5'-TCATTTTTCGTCTTGCGACGT-B | 34 |
| Pre16S 19m 5'JxnD | 5'-TTTGATGCTCAAAGAATTA-F | 35 |
| Pre16S 21m 5'JxnC | 5-S-TCAAACTCTTCAATTTAAAAG | 36 |
| Pre16S 21m R5'Jxn D | 5-F-TCAAACTCTTCAATTTAAAAG | 37 |
| Pre16S 19m R5'JxnC | 5'-TTTGATGCTCAAAGAATTA-S | 38 |
| Pre16S 17m 3'JxnD | 5'-GAGGTGATCCAACCGCA-F | 39 |
| Pre16S 20m 3'JxnC | 5-S-GAACGCTTCTTTAAGGTAAG | 40 |
| Pre16S 20m R3'JxnD | 5-F-GAACGCTTCTTTAAGGTAAG | 41 |
| Pre16S 17m R3'JxnC | 5'-GAGGTGATCCAACCGCA-S | 42 |
| *Pre23S 17m 3'JxnD | 5'-AAGCCTCACGGTTCATT-F | 5 |
| *Pre23S 14m 3'JxnC | 5'-S-GGCGTTGTAAGGTT | 6 |
| Pre23S 14m R3'JxnD | 5'-F-GGCGTTGTAAGGTT | 43 |
| Pre23S 17m R3'JxnC | 5'-AAGCCTCACGGTTCATT-S | 44 |
| Mature rRNA 18m 1484D | 5'-GTTACGACTTCACCCCAG-F | 45 |
| Mature rRNA 19m 1502C | 5'-S-GTTCCCCTACGGTTACCTT | 46 |
| Synthetic Target Oligonucleotides: | | |
| Pre-rRNA 31m 5'-AATGAACCGTGAGGCTTAACCTTACAACGCC | | 47 |
| Mature rRNA 37m 5'-CTGGGGTGAAGTCGTAACAAGGTAACCGTAGGGGAAC | | 48 |

[1]Abbreviations: Number of nucleotides (m), capture probe (C), detector probe (D), splice site (Jxn), reverse orientation (R).
[2]Abbreviations: FITC (F), biotin (B), thiol (S).
*Indicates capture & detector probe pair selected based on its high signal-to-noise ratio.

TABLE 2

Pre- and mature rRNA quantitation during *E. coli* growth phases.

| Timepoint (min) | OD$_{600}$ | CFU/ml | Rate[a] | Doublings[b] | Gen. time[c] | rRNA[d] | pre-rRNA[d] | Ratio | GROWTH PHASE |
|---|---|---|---|---|---|---|---|---|---|
| Overnight Culture | 2.307 | 6.67E+09 | — | — | — | 6,009 | 2 | 2,720 | STATIONARY PHASE |
| 0 | 0 | 5.90E+05 | — | — | — | 5,942 | 110 | 54 | LAG PHASE |
| 30 | 0 | 5.70E+05 | — | — | — | 28,427 | 457 | 62 | |
| 60 | 0.003 | 8.63E+05 | 0.18 | 1.20 | 50.08 | 55,278 | 696 | 79 | LOG PHASE |
| 90 | 0.008 | 2.30E+06 | 0.43 | 2.83 | 21.19 | 78,741 | 970 | 81 | |
| 120 | 0.024 | 6.20E+06 | 0.43 | 2.86 | 21.00 | 91,049 | 1200 | 76 | |
| 150 | 0.068 | 1.91E+07 | 0.49 | 3.24 | 18.51 | 98,782 | 523 | 189 | |
| 180 | 0.175 | 6.53E+07 | 0.53 | 3.55 | 16.88 | 61,571 | 235 | 262 | |

TABLE 2-continued

Pre- and mature rRNA quantitation during *E. coli* growth phases.

| Timepoint (min) | $OD_{600}$ | CFU/ml | Rate[a] | Doublings[b] | Gen. time[c] | rRNA[d] | pre-rRNA[d] | Ratio | GROWTH PHASE |
|---|---|---|---|---|---|---|---|---|---|
| 210 | 0.409 | 2.30E+08 | 0.55 | 3.64 | 16.50 | 38,033 | 208 | 183 | |
| 240 | 0.707 | 5.27E+08 | 0.36 | 2.39 | 25.14 | 29,801 | 114 | 260 | EARLY |
| 270 | 1.095 | 1.17E+09 | 0.35 | 2.30 | 26.14 | 19,610 | 42 | 466 | STATIONARY |
| 300 | 1.466 | 2.33E+09 | 0.30 | 2.00 | 30.00 | 13,162 | 25 | 536 | PHASE |
| 330 | 1.686 | 3.23E+09 | 0.14 | 0.94 | 63.74 | 7,608 | 11 | 665 | STATIONARY |
| 360 | 1.834 | 4.43E+09 | 0.14 | 0.91 | 65.87 | 5,734 | 8 | 723 | PHASE |
| 390 | 1.957 | 5.03E+09 | 0.06 | 0.37 | 163.81 | 4,899 | 7 | 706 | |
| 420 | 2.051 | 5.73E+09 | 0.06 | 0.38 | 159.68 | 6,230 | 6 | 1,049 | |

[a]Growth rate in log units per 30 min.
[b]Doublings per hour.
[c]Generation time (min).
[d]Copies per cell.

Discussion

We describe an electrochemical sensor assay for detection and quantitation of pre-rRNA. Pre-rRNA represents a labile pool of rRNA precursor molecules produced during rRNA transcription. Pre-rRNA differs from mature rRNA by the presence of 5' and 3' tails that are removed during the maturation process. Because pre-rRNA represents a relatively small fraction (0.1%-10%) of total rRNA, a sensitive assay is required for its detection. To achieve the needed sensitivity, our electrochemical Au-sensor assay relies on the use of a ternary interface involving hexanedithiol co-immobilized with a thiolated capture probe, followed by the incorporation of 6-mercapto-1-hexanol as diluent. This new interface has been shown to offer a greatly improved surface blocking and maximal hybridization efficiency allowing ultrasensitive electrochemical detection of target nucleic acids (2, 8, 17). Direct nucleic acid detection methods, such as the electrochemical sandwich hybridization assay described herein, have inherent advantages over methods that require target amplification, such as qRT-PCR. We were able to quantitate pre-rRNA during different *E. coli* growth phases, and documented dramatic shifts in copy number from 2 to 1,200 copies per cell in the stationary and log phases of growth, respectively. This is the first time that pre-rRNA copy numbers per cell have been quantitated electrochemically. The 600-fold increase in pre-rRNA copy number that we observed is considerably larger than the 50-fold increase reported by Cangelosi et al (3) using luminescence detection. Possible reasons for this difference include a low limit of detection and the *E. coli* strain type. Cangelosi et al examined the *E. coli* type strain ATCC 11775, which was isolated in 1895 by Migula, and may have undergone metabolic changes during passage. In contrast, our studies were performed on a recently isolated wild-type uropathogenic *E. coli* strain with a relatively fast peak doubling time of 16.5 minutes.

Antibiotics differ in their effects on pre-rRNA and mature rRNA. Rifampicin is an inhibitor of prokaryotic DNA-dependent RNA polymerase. Because pre-rRNA is rapidly processed to mature rRNA, inhibiting transcription quickly reduces the pool of pre-rRNA, especially during the log phase of growth. In contrast, chloramphenicol and gentamicin are protein synthesis inhibitors. Chloramphenicol acts by binding to the 23S subunit of bacterial ribosomes to inhibit protein synthesis, whereas gentamicin acts by inhibiting the proof-reading function of ribosomes, thereby introducing translation errors and premature peptide chain termination events. In either case, these protein synthesis inhibitors should not directly interfere with pre-rRNA synthesis. Accordingly, we observed a decrease in the pool of mature rRNA, presumably because of the loss of proteins required for ribosome formation and stability. In the case of chloramphenicol, inhibition of pre-rRNA processing not only resulted in a decrease of mature rRNA but an increase in pre-rRNA (FIG. 5B).

Ciprofloxacin is a quinolone antibiotic that inhibits the activity of DNA gyrase, the bacterial topoisomerase that introduces and relaxes DNA supercoils. Relaxing of supercoils is required for unpackaging of DNA prior to not only DNA replication but also RNA transcription (16). As in the case of rifampicin, inhibition of RNA transcription by ciprofloxacin resulted in a rapid decrease in pre-rRNA, detectable within fifteen minutes after addition of the antibiotic. Quinolone resistance typically results from gyrase mutations that prevent binding of the quinolone to the gyrase. As expected, addition of ciprofloxacin had no discernable effect of pre-rRNA levels in ciprofloxacin resistant organisms (FIG. 6).

There is a considerable interest in methods for determining the susceptibility of bacteria in clinical specimens in a time frame sufficient to impact clinical decision making. A major drawback of current clinical bacteriology methods is the need to isolate bacteria on solid agar media when processing a clinical specimen. In the absence of expeditious antibiotic susceptibility testing, clinicians typically initiate "empiric" antibiotic treatment, meaning that antibiotics are chosen based on prior knowledge of potential organisms and their antibiotic resistance patterns. Empiric antibiotics for bacteremia are typically broad-spectrum to treat a wide variety of possible bacterial pathogens. This approach is especially problematic in the management of complex urinary tract infections where quinolone-resistance rates are typically 20-30% (5). In addition, overuse of broad-spectrum antibiotics contributes to the emergence of antibiotic resistance by applying selective pressure to the patient's flora and favoring colonization by resistant organisms.

To address the need for antibiotic resistance data at the time of initial antibiotic selection, methods are needed to analyze the antibiotic susceptibility of organisms in clinical specimens. The electrochemical sensor assay has been validated on human clinical urine specimens from patients with urinary tract infection (9, 11). Electrochemical sensor assays for pre-rRNA would be expected to be useful for identifying bacteria that are susceptible to antibiotics such as rifampicin and ciprofloxacin that directly or indirectly inhibit RNA transcription. It may be possible to extend this approach for antibiotic susceptibility testing to other drugs by first depleting pre-rRNA levels and then measuring the ability of the antibiotic to inhibit pre-rRNA replenishment (4). However, because antibiotics act by widely divergent mechanisms, various approaches may be necessary to achieve comprehensive antibiotic susceptibility testing. For example, we have successfully applied ATP bioluminescence to determine antimicrobial susceptibility of uropathogens within 120 min after inoculation of clinical urine specimens into growth medium with and without antibiotics (7). Application of such assays to bacteria in clinical specimens at the point of care would enable patient-specific antibiotic therapy.

Example 2

Use of pre-rRNA to Assess Growth Phase of Bacteria

Figure 7:
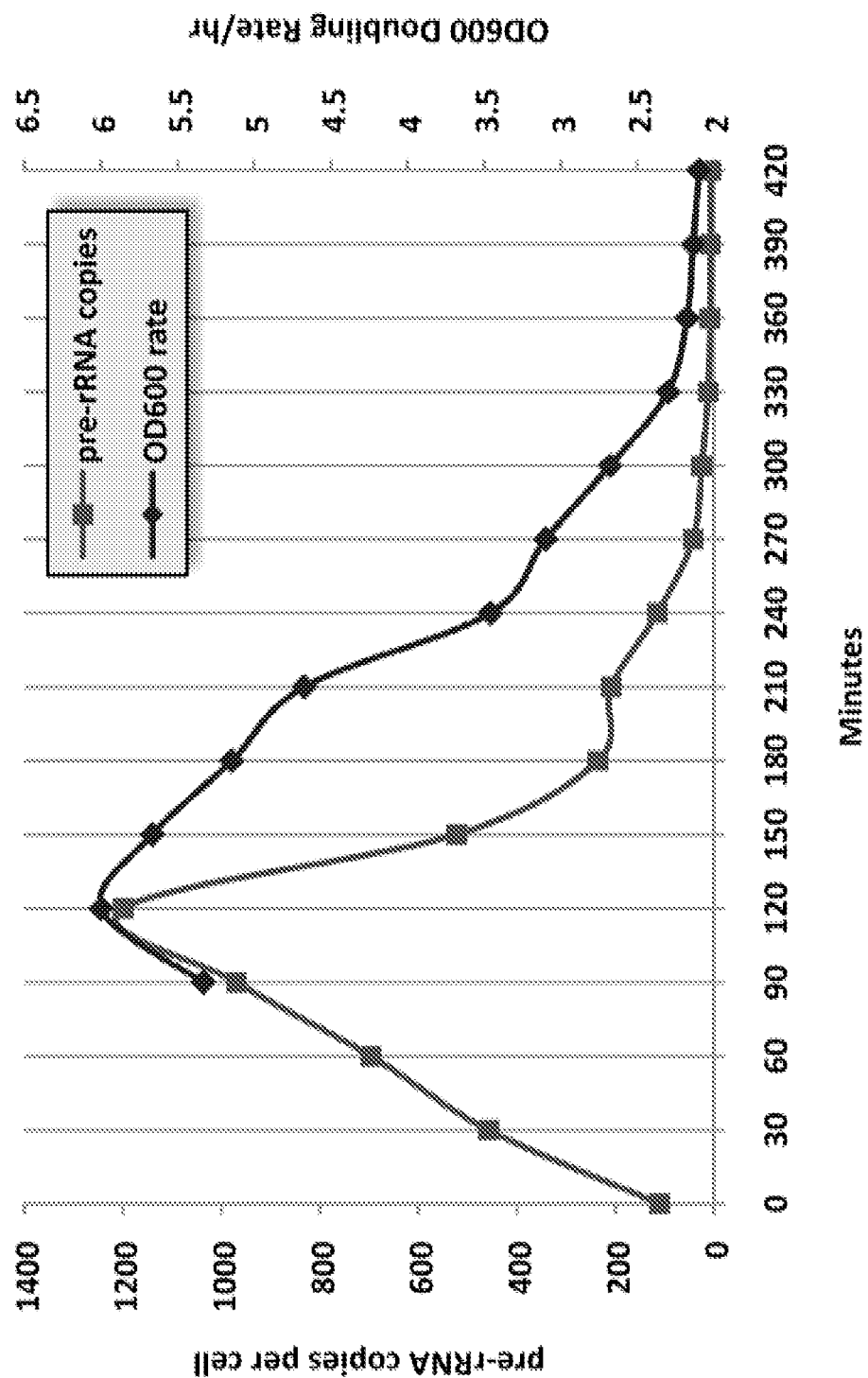
FIG. 7. Graph depicting the correlation between pre-rRNA copies per cell and bacterial growth rate. Growth rate is based on total cell volume as measured by turbidity or the increase in optical density at 600 nm, which peaks at 120 minutes, the same time as the peak in number of prRNA copies per cell.
Figure 8:
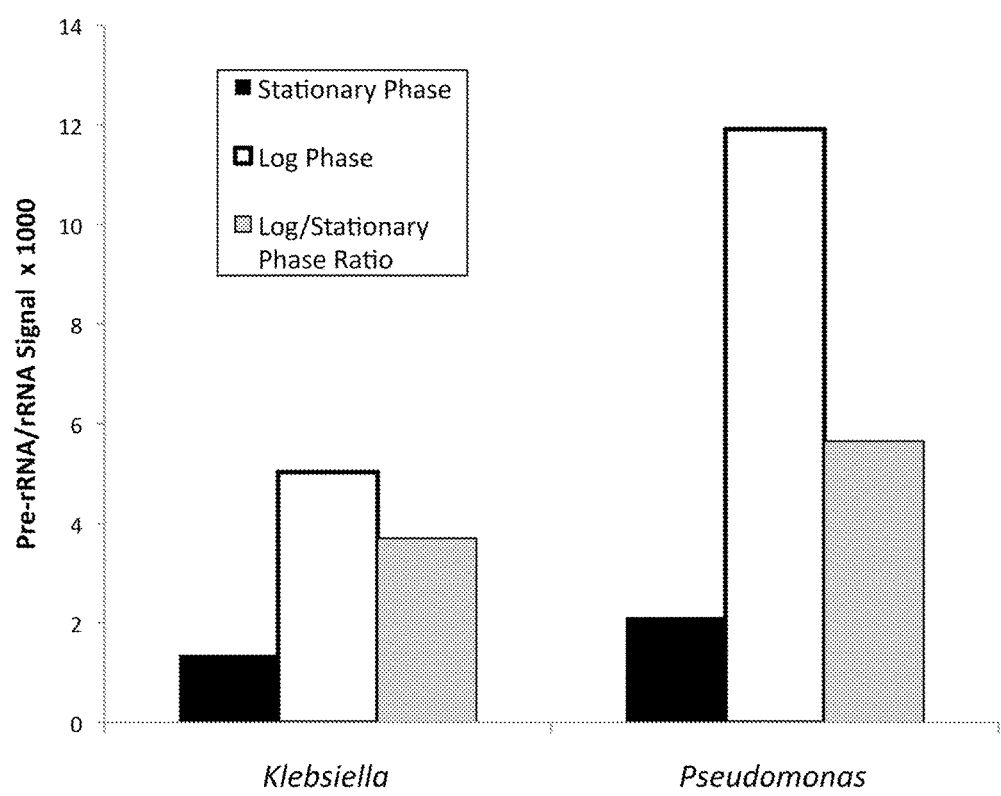
FIG. 8. Evaluation of pre-rRNA probe pairs in gram-negative bacteria. The ratio of signals from probe pairs specific for pre-rRNA to mature rRNA were compared in overnight (O/N) or stationary phase cultures vs. cultures in the log phase of growth. Pre-rRNA signals were four-fold higher in log phase *Klebsiella* cells than in stationary phase *Klebsiella* cells, and six-fold higher in log phase *Pseudomonas* cells than in stationary phase *Pseudomonas* cells.
Figure 9:
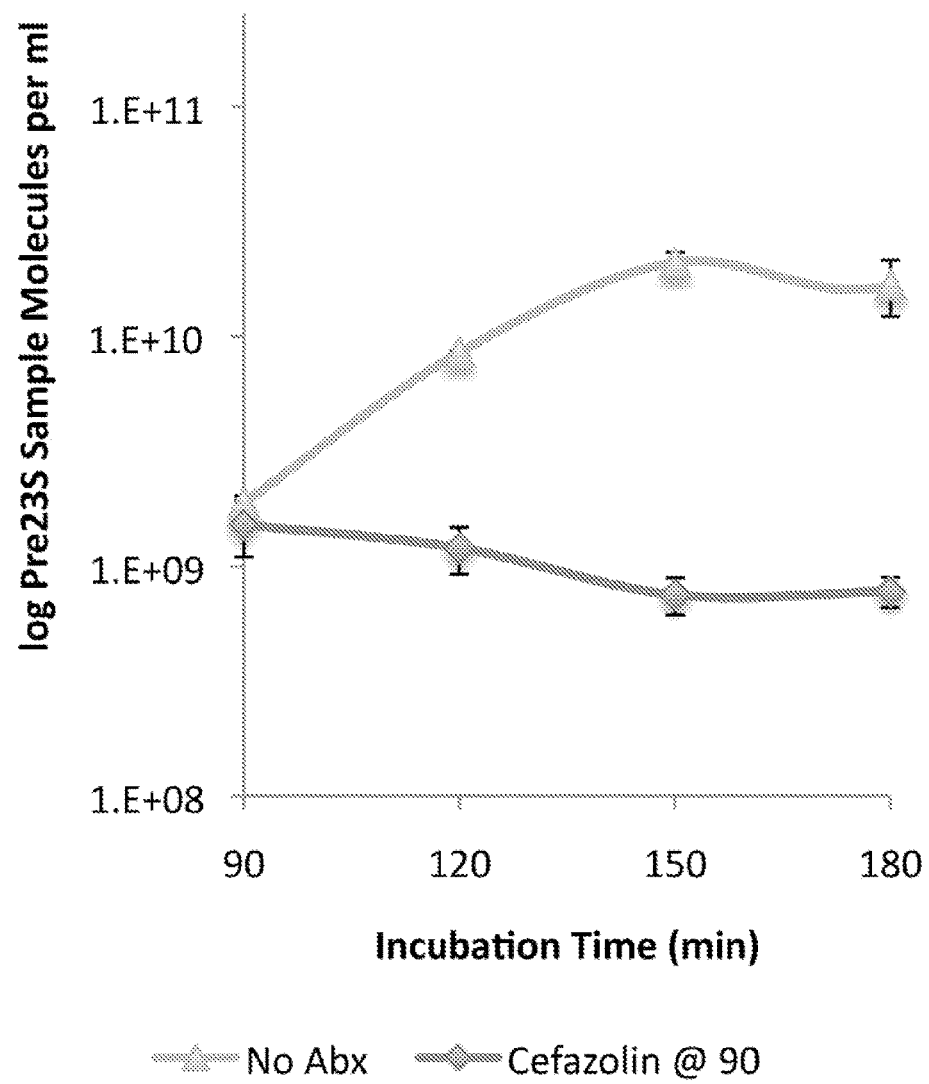
FIG. 9. Response of pre-rRNA to cefazolin. Addition of cefazolin to a culture of a susceptible strain of *E. coli* in the log phase of growth resulted in a one-log drop in the amount pre-rRNA within 30 min compared to a culture without the antibiotic. Errors bars estimated the standard deviation.

The correlation between pre-rRNA copies per cell and bacterial growth rate is depicted in FIG. 7. Growth rate is based on total cell volume as measured by turbidity or the increase in optical density at 600 nm, which peaks at 120 minutes, the same time as the peak in number of prRNA copies per cell. FIG. 8 illustrates the evaluation of pre-rRNA probe pairs in gram-negative bacteria. The ratio of signals from probe pairs specific for pre-rRNA to mature rRNA were compared in overnight (O/N) or stationary phase cultures and in cultures in the log phase of growth. Pre-rRNA signals were four-fold higher in log phase *Klebsiella* cells than in stationary phase *Klebsiella* cells, and six-fold higher in log phase *Pseudomonas* cells than in stationary phase *Pseudomonas* cells. FIG. 9 shows the response of pre-rRNA to cefazolin. Addition of cefazolin, a beta-lactam antibiotic, to a culture of a susceptible strain of *E. coli* in the log phase of growth resulted in a one-log drop in the amount pre-rRNA within 30 min compared to a culture without the antibiotic. Errors bars estimated the standard deviation.

REFERENCES

1. Bremner, H., and P. P. Dennis. 1996. Modulation of chemical composition and other parameters of the cell by growth rate, p. 1553-1569. In F. C. Neidhardt (ed.), *Escherichia coli* and *Salmonella*, vol. 2. ASM Press, Washington, D.C.
2. Campuzano, S., et al. 2011. Biosens Bioelectron 26:3577-3584.
3. Cangelosi, G. A., and W. H. Barbant. 1997. J Bacteriol 179:4457-4463.
4. Cangelosi, G. A., et al. 1996. Antimicrob Agents Chemother 40:1790-1795.
5. Cullen, et al. 2011. Br J Urol Int [Epub ahead of print].
6. Fuchs, B. M., et al. 1998. Appl Environ Microbiol 64:4973-4982.
7. Ivancic, V., et al. 2008. J Clin Microbiol 46:1213-1219.
8. Kuralay, F., et al. 2011. Talanta 85:1330-1337.
9. Liao, J. C., et al. 2006. J Clin Microbiol 44:561-570.
10. Liao, J. C., et al. 2007. J Mol Diagn 9:158-168.
11. Mach, K. E., et al. 2009. J Urol 182:2735-2741.
12. Mastali, M., et al. 2008. J Clin Microbiol 46:2707-2716.
13. Sun, C. P., et al. 2005. Mol Genet Metab 84:90-99.
14. Wang, J. 2006. Analytical Electrochemistry. J. Wiley, New York.
15. Wang, J. 2008. Electrochemical glucose biosensors. Chem Rev 108:814-825.
16. Willmott, C. J., et al. 1994. J Mol Biol 242:351-363.
17. Wu, J., et al. 2010. Anal Chem 82:8830-8837.
18. Wu, J., et al. 2009. Anal Chem 81:10007-10012.

Those skilled in the art will appreciate that the conceptions and specific embodiments disclosed in the foregoing description may be readily utilized as a basis for modifying or designing other embodiments for carrying out the same purposes of the present invention. While the above is a complete description of the preferred embodiments of the invention, various alternatives, modifications, and equivalents may be used. Therefore, the above description should not be taken as limiting the scope of the invention which is defined by the appended claims.

What is claimed is:

1. A device for detecting intact pre-rRNA in a bacterial sample, the device comprising a pair of oligonucleotide probes, at least one of which is immobilized on a solid support, wherein the pair of oligonucleotide probes comprises an oligonucleotide probe up to 50 nucleotides in length that includes SEQ ID NO: 5 and an oligonucleotide probe up to 50 nucleotides in length that includes SEQ ID NO: 6, and wherein the pair of oligonucleotide probes selectively hybridizes to a target sequence specific to intact pre-rRNA, wherein the target sequence comprises contiguous nucleotides of bacterial ribosomal RNA (rRNA) spanning a splice site between pre-ribosomal RNA (prRNA) tail and mature ribosomal RNA (mRNA).

2. The device of claim 1, wherein the bacterial rRNA is 23S rRNA.

3. The device of claim 1, wherein the target sequence is:

(a)

(SEQ ID NO: 1)
AATGAACCGTGAGGCTT|AACCTTACAACGCCGAAGCTGTTTTGGCGG
ATTG;

(b)
(c)
(d)

wherein | indicates the splice site between prRNA and mRNA.

4. The device of claim 1, wherein the oligonucleotide pair of probes is labeled with a detectable marker.

5. The device of claim 4, wherein the marker is selected from the group consisting of fluorescent label, a radioactive label, a luminescent label, an enzyme, biotin, thiol or a dye.

6. The device of claim 1, wherein the solid support is an electrode, membrane, ELISA well, or optical surface.

7. The device of claim 1, wherein at least one of the oligonucleotide probes is modified to contain a phosphorothioate or 2' 0-methyl linkage, a nontraditional base, and/or a modified form of adenine, cytidine, guanine, thymine, or uridine.

8. The device of claim 1, wherein the pair of probes hybridizes to the target sequence under highly stringent conditions.

9. A method for determining whether a sample of bacteria is susceptible to an antibiotic agent, the method comprising the steps of:

(a) contacting a specimen obtained from the sample with the device of claim 1 in the absence of the agent;

(b) contacting a specimen obtained from the sample with the device in the presence of the antibiotic agent;

(c) detecting the relative amounts of probe hybridization to the target sequence in the specimens of (a) and (b);

(d) identifying the sample as susceptible to antibiotic treatment if the amount of probe hybridization to the target sequence in step (b) is reduced by at least 80% relative to the amount of probe hybridization to the target sequence in step (a).

10. The method of claim 9, further comprising inoculating the specimen into a growth medium prior to the contacting of steps (a) and (b).

11. The method of claim 9, wherein no pre-treatment of the specimen to deplete prRNA is performed prior to the contacting of steps (a) or (b).

12. The method of claim 1, wherein the detecting comprises an optical, electrochemical or immunological assay.

13. The method of claim 12, wherein the detecting comprises an electrochemical assay.

14. The method of claim 9, further comprising lysing the bacteria under conditions that release rRNA from the bacteria prior to the contacting of steps (a) and (b).

15. The method of claim 9, wherein the antibiotic agent is Chloramphenicol, aminoglycosides, quinolones, or beta-lactam antibiotics.

16. A method for determining the antibiotic efficacy of a candidate antibiotic agent, the method comprising the steps of:

(a) contacting a specimen obtained from the sample with the device of claim 1 in the absence of the agent;

(b) contacting a specimen obtained from the sample with the device in the presence of the agent;

(c) detecting the relative amounts of probe hybridization to the target sequence in the specimens of (a) and (b);

(d) identifying the agent as effective if the amount of probe hybridization to the target sequence in step (b) is reduced by at least 80% relative to the amount of probe hybridization to the target sequence in step (a).

17. A method for monitoring the growth rate of a bacterial culture, the method comprising the steps of:

(a) contacting a specimen obtained from the culture with the device of claim 1;

(b) detecting the amount of probe hybridization to the target sequence in the specimen of (a) relative to an earner time point:

(c) identifying the culture as growing if the amount of probe hybridization to the target sequence in step (b) is increased relative to the amount of probe hybridization to the target sequence at the earner time point.

* * * * *

UNITED STATES PATENT AND TRADEMARK OFFICE
CERTIFICATE OF CORRECTION

PATENT NO. : 10,370,728 B2  
APPLICATION NO. : 14/398725  
DATED : August 6, 2019  
INVENTOR(S) : Haake et al.

Page 1 of 1

It is certified that error appears in the above-identified patent and that said Letters Patent is hereby corrected as shown below:

In the Claims

Column 39, Line 32, delete "(a)"; Line 40, delete "(b)"; Line 41, delete "(c)"; and Line 42, delete "(d)".

Column 39, Line 37, replace "I" with --|--.

Column 40, Lines 58 and 62, each occurrence of "earner" should read --earlier--.

Signed and Sealed this  
Twenty-sixth Day of November, 2019

Andrei Iancu  
*Director of the United States Patent and Trademark Office*

SEQUENCE LISTING

```
<160> NUMBER OF SEQ ID NOS: 50

<210> SEQ ID NO 1
<211> LENGTH: 51
<212> TYPE: DNA
<213> ORGANISM: Escherichia coli

<400> SEQUENCE: 1
aatgaaccgt gaggcttaac cttacaacgc cgaagctgtt ttggcggatt g            51

<210> SEQ ID NO 2
<211> LENGTH: 50
<212> TYPE: DNA
<213> ORGANISM: Pseudomonas aeruginosa

<400> SEQUENCE: 2
aattgcccgt gaggcttgac catataacac ccaaacaatc tgacgattgt              50

<210> SEQ ID NO 3
<211> LENGTH: 53
<212> TYPE: DNA
<213> ORGANISM: Streptococcus pyogenes

<400> SEQUENCE: 3
```

```
aatagctcga ggacttatcc aaaaagaaat attgacaacg ttacggattc ttg        53

<210> SEQ ID NO 4
<211> LENGTH: 51
<212> TYPE: DNA
<213> ORGANISM: Staphylococcus aureus

<400> SEQUENCE: 4
aatcgatcga agacttaatc aaaataaatg ttttgcgaag caaaatcact t          51

<210> SEQ ID NO 5
<211> LENGTH: 17
<212> TYPE: DNA
<213> ORGANISM: Artificial Sequence
<220> FEATURE:
<223> OTHER INFORMATION: Synthetic Probe

<400> SEQUENCE: 5
aagcctcacg gttcatt                                                17

<210> SEQ ID NO 6
<211> LENGTH: 14
<212> TYPE: DNA
<213> ORGANISM: Artificial Sequence
<220> FEATURE:
<223> OTHER INFORMATION: Synthetic Probe

<400> SEQUENCE: 6
ggcgttgtaa ggtt                                                   14

<210> SEQ ID NO 7
<211> LENGTH: 17
<212> TYPE: DNA
<213> ORGANISM: Artificial Sequence
<220> FEATURE:
<223> OTHER INFORMATION: Synthetic Probe

<400> SEQUENCE: 7
aagcctcacg ggcaatt                                                17

<210> SEQ ID NO 8
<211> LENGTH: 14
<212> TYPE: DNA
<213> ORGANISM: Artificial Sequence
<220> FEATURE:
<223> OTHER INFORMATION: Synthetic Probe

<400> SEQUENCE: 8
ggtgttatat ggtc                                                   14

<210> SEQ ID NO 9
<211> LENGTH: 16
<212> TYPE: DNA
<213> ORGANISM: Artificial Sequence
<220> FEATURE:
<223> OTHER INFORMATION: Synthetic Probe

<400> SEQUENCE: 9
aagtcctcga gctatt                                                 16

<210> SEQ ID NO 10
<211> LENGTH: 14
<212> TYPE: DNA
<213> ORGANISM: Artificial Sequence
<220> FEATURE:
<223> OTHER INFORMATION: Synthetic Probe
```

```
<400> SEQUENCE: 10 atttctttt ggat                                                    14

<210> SEQ ID NO 11
<211> LENGTH: 16
<212> TYPE: DNA
<213> ORGANISM: Artificial Sequence
<220> FEATURE:
<223> OTHER INFORMATION: Synthetic Probe

<400> SEQUENCE: 11
aagtcttcga tcgatt                                                 16

<210> SEQ ID NO 12
<211> LENGTH: 14
<212> TYPE: DNA
<213> ORGANISM: Artificial Sequence
<220> FEATURE:
<223> OTHER INFORMATION: Synthetic Probe

<400> SEQUENCE: 12
catttatttt gatt                                                   14

<210> SEQ ID NO 13
<211> LENGTH: 15
<212> TYPE: DNA
<213> ORGANISM: Artificial Sequence
<220> FEATURE:
<223> OTHER INFORMATION: Synthetic Probe

<400> SEQUENCE: 13
tttttcgtct tgcga                                                  15

<210> SEQ ID NO 14
<211> LENGTH: 15
<212> TYPE: DNA
<213> ORGANISM: Artificial Sequence
<220> FEATURE:
<223> OTHER INFORMATION: Synthetic Probe

<400> SEQUENCE: 14
gagacttggt attca                                                  15

<210> SEQ ID NO 15
<211> LENGTH: 15
<212> TYPE: DNA
<213> ORGANISM: Artificial Sequence
<220> FEATURE:
<223> OTHER INFORMATION: Synthetic Probe

<400> SEQUENCE: 15
gagacttggt attca                                                  15

<210> SEQ ID NO 16
<211> LENGTH: 15
<212> TYPE: DNA
<213> ORGANISM: Artificial Sequence
<220> FEATURE:
<223> OTHER INFORMATION: Synthetic Probe

<400> SEQUENCE: 16
tttttcgtct tgcga                                                  15

<210> SEQ ID NO 17
```

```
<211> LENGTH: 17
<212> TYPE: DNA
<213> ORGANISM: Artificial Sequence
<220> FEATURE:
<223> OTHER INFORMATION: Synthetic Probe

<400> SEQUENCE: 17
ttgagacttg gtattca                                                    17

<210> SEQ ID NO 18
<211> LENGTH: 17
<212> TYPE: DNA
<213> ORGANISM: Artificial Sequence
<220> FEATURE:
<223> OTHER INFORMATION: Synthetic Probe

<400> SEQUENCE: 18
tttttcgtct tgcgacg                                                    17

<210> SEQ ID NO 19
<211> LENGTH: 19
<212> TYPE: DNA
<213> ORGANISM: Artificial Sequence
<220> FEATURE:
<223> OTHER INFORMATION: Synthetic Probe

<400> SEQUENCE: 19
tcttgagact tggtattca                                                  19

<210> SEQ ID NO 20
<211> LENGTH: 19
<212> TYPE: DNA
<213> ORGANISM: Artificial Sequence
<220> FEATURE:
<223> OTHER INFORMATION: Synthetic Probe

<400> SEQUENCE: 20
tttttcgtct tgcgacgtt                                                  19

<210> SEQ ID NO 21
<211> LENGTH: 21
<212> TYPE: DNA
<213> ORGANISM: Artificial Sequence
<220> FEATURE:
<223> OTHER INFORMATION: Synthetic Probe

<400> SEQUENCE: 21
actcttgaga cttggtattc a                                               21

<210> SEQ ID NO 22
<211> LENGTH: 21
<212> TYPE: DNA
<213> ORGANISM: Artificial Sequence
<220> FEATURE:
<223> OTHER INFORMATION: Synthetic Probe

<400> SEQUENCE: 22
tttttcgtct tgcgacgtta a                                               21

<210> SEQ ID NO 23
<211> LENGTH: 17
<212> TYPE: DNA
<213> ORGANISM: Artificial Sequence
<220> FEATURE:
<223> OTHER INFORMATION: Synthetic Probe

<400> SEQUENCE: 23
```
agacttggta ttcattt                                                    17

<210> SEQ ID NO 24
<211> LENGTH: 17
<212> TYPE: DNA
<213> ORGANISM: Artificial Sequence
<220> FEATURE:
<223> OTHER INFORMATION: Synthetic Probe

<400> SEQUENCE: 24
ttcgtcttgc gacgtta                                                    17

<210> SEQ ID NO 25
<211> LENGTH: 19
<212> TYPE: DNA
<213> ORGANISM: Artificial Sequence
<220> FEATURE:
<223> OTHER INFORMATION: Synthetic Probe

<400> SEQUENCE: 25
tgagacttgg tattcattt                                                  19

<210> SEQ ID NO 26
<211> LENGTH: 19
<212> TYPE: DNA
<213> ORGANISM: Artificial Sequence
<220> FEATURE:
<223> OTHER INFORMATION: Synthetic Probe

<400> SEQUENCE: 26
ttcgtcttgc gacgttaag                                                  19

<210> SEQ ID NO 27
<211> LENGTH: 21
<212> TYPE: DNA
<213> ORGANISM: Artificial Sequence
<220> FEATURE:
<223> OTHER INFORMATION: Synthetic Probe

<400> SEQUENCE: 27
cttgagactt ggtattcatt t                                               21

<210> SEQ ID NO 28
<211> LENGTH: 21
<212> TYPE: DNA
<213> ORGANISM: Artificial Sequence
<220> FEATURE:
<223> OTHER INFORMATION: Synthetic Probe

<400> SEQUENCE: 28
ttcgtcttgc gacgttaaga a                                               21

<210> SEQ ID NO 29
<211> LENGTH: 17
<212> TYPE: DNA
<213> ORGANISM: Artificial Sequence
<220> FEATURE:
<223> OTHER INFORMATION: Synthetic Probe

<400> SEQUENCE: 29
ctcttgagac ttggtat                                                    17

<210> SEQ ID NO 30
<211> LENGTH: 18
<212> TYPE: DNA

<210> SEQ ID NO 30
<211> LENGTH: 18
<212> TYPE: DNA
<213> ORGANISM: Artificial Sequence
<220> FEATURE:
<223> OTHER INFORMATION: Synthetic Probe

<400> SEQUENCE: 30 tcattttcg tcttgcgb                                              18

<210> SEQ ID NO 31
<211> LENGTH: 19
<212> TYPE: DNA
<213> ORGANISM: Artificial Sequence
<220> FEATURE:
<223> OTHER INFORMATION: Synthetic Probe

<400> SEQUENCE: 31
cactcttgag acttggtat                                            19

<210> SEQ ID NO 32
<211> LENGTH: 19
<212> TYPE: DNA
<213> ORGANISM: Artificial Sequence
<220> FEATURE:
<223> OTHER INFORMATION: Synthetic Probe

<400> SEQUENCE: 32 tcattttcg tcttgcgac                                             19

<210> SEQ ID NO 33
<211> LENGTH: 21
<212> TYPE: DNA
<213> ORGANISM: Artificial Sequence
<220> FEATURE:
<223> OTHER INFORMATION: Synthetic Probe

<400> SEQUENCE: 33
ttcactcttg agacttggta t                                         21

<210> SEQ ID NO 34
<211> LENGTH: 21
<212> TYPE: DNA
<213> ORGANISM: Artificial Sequence
<220> FEATURE:
<223> OTHER INFORMATION: Synthetic Probe

<400> SEQUENCE: 34 tcattttcg tcttgcgacg t                                          21

<210> SEQ ID NO 35
<211> LENGTH: 19
<212> TYPE: DNA
<213> ORGANISM: Artificial Sequence
<220> FEATURE:
<223> OTHER INFORMATION: Synthetic Probe

<400> SEQUENCE: 35
tttgatgctc aaagaatta                                            19

<210> SEQ ID NO 36
<211> LENGTH: 21
<212> TYPE: DNA
<213> ORGANISM: Artificial Sequence
<220> FEATURE:
<223> OTHER INFORMATION: Synthetic Probe

<400> SEQUENCE: 36
tcaaactctt caatttaaaa g                                         21

<210> SEQ ID NO 37
<211> LENGTH: 21
<212> TYPE: DNA
<213> ORGANISM: Artificial Sequence
<220> FEATURE:
<223> OTHER INFORMATION: Synthetic Probe

<400> SEQUENCE: 37
tcaaactctt caatttaaaa g                                              21

<210> SEQ ID NO 38
<211> LENGTH: 19
<212> TYPE: DNA
<213> ORGANISM: Artificial Sequence
<220> FEATURE:
<223> OTHER INFORMATION: Synthetic Probe

<400> SEQUENCE: 38
tttgatgctc aaagaatta                                                 19

<210> SEQ ID NO 39
<211> LENGTH: 17
<212> TYPE: DNA
<213> ORGANISM: Artificial Sequence
<220> FEATURE:
<223> OTHER INFORMATION: Synthetic Probe

<400> SEQUENCE: 39
gaggtgatcc aaccgca                                                   17

<210> SEQ ID NO 40
<211> LENGTH: 20
<212> TYPE: DNA
<213> ORGANISM: Artificial Sequence
<220> FEATURE:
<223> OTHER INFORMATION: Synthetic Probe

<400> SEQUENCE: 40
gaacgcttct ttaaggtaag                                                20

<210> SEQ ID NO 41
<211> LENGTH: 20
<212> TYPE: DNA
<213> ORGANISM: Artificial Sequence
<220> FEATURE:
<223> OTHER INFORMATION: Synthetic Probe

<400> SEQUENCE: 41
gaacgcttct ttaaggtaag                                                20

<210> SEQ ID NO 42
<211> LENGTH: 17
<212> TYPE: DNA
<213> ORGANISM: Artificial Sequence
<220> FEATURE:
<223> OTHER INFORMATION: Synthetic Probe

<400> SEQUENCE: 42
gaggtgatcc aaccgca                                                   17

<210> SEQ ID NO 43
<211> LENGTH: 14
<212> TYPE: DNA
<213> ORGANISM: Artificial Sequence
<220> FEATURE:

<223> OTHER INFORMATION: Synthetic Probe

<400> SEQUENCE: 43
ggcgttgtaa ggtt                                            14

<210> SEQ ID NO 44
<211> LENGTH: 17
<212> TYPE: DNA
<213> ORGANISM: Artificial Sequence
<220> FEATURE:
<223> OTHER INFORMATION: Synthetic Probe

<400> SEQUENCE: 44
aagcctcacg gttcatt                                         17

<210> SEQ ID NO 45
<211> LENGTH: 18
<212> TYPE: DNA
<213> ORGANISM: Artificial Sequence
<220> FEATURE:
<223> OTHER INFORMATION: Synthetic Probe

<400> SEQUENCE: 45
gttacgactt caccccag                                        18

<210> SEQ ID NO 46
<211> LENGTH: 19
<212> TYPE: DNA
<213> ORGANISM: Artificial Sequence
<220> FEATURE:
<223> OTHER INFORMATION: Synthetic Probe

<400> SEQUENCE: 46
gttcccctac ggttaccTt                                       19

<210> SEQ ID NO 47
<211> LENGTH: 31
<212> TYPE: DNA
<213> ORGANISM: Artificial Sequence
<220> FEATURE:
<223> OTHER INFORMATION: Synthetic Probe

<400> SEQUENCE: 47
aatgaaccgt gaggcttaac cttacaacgc c                         31

<210> SEQ ID NO 48
<211> LENGTH: 37
<212> TYPE: DNA
<213> ORGANISM: Artificial Sequence
<220> FEATURE:
<223> OTHER INFORMATION: synthetic probe

<400> SEQUENCE: 48
ctggggtgaa gtcgtaacaa ggtaaccgta ggggaac                   37

<210> SEQ ID NO 49
<211> LENGTH: 155
<212> TYPE: RNA
<213> ORGANISM: Escherichia coli

<400> SEQUENCE: 49
aguuugagaa guuaauuuuc aaacugcgag uuucuuaauu ugaagcauua cuuaaugcac    60
aagugagaac ucugaaccau aaguaaaaag cagaacgcug caauucuuag gcauagaagc   120
ucacgcguga uguuucaugc gaagaaauuc cauuc                             155

```
<210> SEQ ID NO 50
<211> LENGTH: 64
<212> TYPE: RNA
<213> ORGANISM: Escherichia coli

<400> SEQUENCE: 50
cgaaucagcg aauuggagug ggcuucuaca aauuugucga agccgcauuc caauucggag     60
ugcc                                                                 64
```